US010045526B2

(12) United States Patent
Coelho

(10) Patent No.: US 10,045,526 B2
(45) Date of Patent: Aug. 14, 2018

(54) METHOD AND APPARATUS FOR CRYOPRESERVATION OF BLOOD CELLS IN A STERILE ENVIRONMENT

(71) Applicant: SynGen Inc., Sacramento, CA (US)

(72) Inventor: Philip H. Coelho, Sacramento, CA (US)

(73) Assignee: Thermogenesis Corp., Rancho Cordova, CA (US)

(*) Notice: Subject to any disclaimer, the term of this patent is extended or adjusted under 35 U.S.C. 154(b) by 366 days.

(21) Appl. No.: 14/917,872

(22) PCT Filed: Sep. 9, 2014

(86) PCT No.: PCT/US2014/054656
§ 371 (c)(1),
(2) Date: Mar. 9, 2016

(87) PCT Pub. No.: WO2015/038494
PCT Pub. Date: Mar. 19, 2015

(65) Prior Publication Data
US 2016/0219869 A1 Aug. 4, 2016

Related U.S. Application Data

(60) Provisional application No. 61/876,168, filed on Sep. 10, 2013.

(51) Int. Cl.
*A01N 1/02* (2006.01)
*C12M 1/00* (2006.01)
*A61M 1/02* (2006.01)

(52) U.S. Cl.
CPC .......... *A01N 1/0252* (2013.01); *A01N 1/0268* (2013.01); *A01N 1/0284* (2013.01); *C12M 45/22* (2013.01); *A61M 1/0272* (2013.01)

(58) Field of Classification Search
CPC .... C12M 45/22; A01N 1/0252; A01N 1/0284; A01N 1/0268; A61M 1/0272
See application file for complete search history.

(56) References Cited

U.S. PATENT DOCUMENTS 5,769,839 A * 6/1998 Carmen et al. .......... A01N 1/02
128/898
8,066,127 B2 * 11/2011 Coelho et al. ...... A61M 1/0272
210/103

(Continued)

FOREIGN PATENT DOCUMENTS

DE 102011105311 A1 12/2012

*Primary Examiner* — Gautam Prakash
(74) *Attorney, Agent, or Firm* — Temmerman Law Office; Mathew J. Temmerman

(57) ABSTRACT

An apparatus and related method for the optimization of the cryopreservation of various types of cells, including but not limited to hematopoietic and mesenchymal stem and progenitor cells, and endothelial progenitor cells found in normal blood, placental/cord blood, bone marrow or the stromal vascular fraction of adipose tissue. The apparatus for cryopreservation of biological materials in a sterile environment comprises a cryopreservation workstation, a rigid disposable cartridge, and a freezing bag assembly. The apparatus and related method provide for the precise, temperature controlled, homogenously distributed introduction of a cryoprotectant containing dimethyl sulfoxide (DMSO) into a solution containing nucleated cells in a manner that provides a safe increase in osmotic pressure and a controlled release of exothermic heat within the cells as the DMSO penetrates the cell membrane and replaces water molecules prior to the freezing of the cells.

8 Claims, 18 Drawing Sheets

(56) References Cited

U.S. PATENT DOCUMENTS

2007/0269887 A1* 11/2007 Coelho ............... A61M 1/0209
435/366
2013/0029370 A1* 1/2013 Coelho et al. ...... A61M 1/3693
435/29

* cited by examiner

METHOD AND APPARATUS FOR CRYOPRESERVATION OF BLOOD CELLS IN A STERILE ENVIRONMENT

RELATED APPLICATIONS

This application claims priority under 35 U.S.C § 371 to PCT application No. PCT/US2014/054656, filed Sep. 9, 2014, which claims the benefit of U.S. provisional application Ser. No. 61/876168 filed on Sep. 10, 2013. The disclosure of these applications is incorporated herein as if set out in full.

BACKGROUND OF THE DISCLOSURE

Technical Field of the Disclosure

The method and apparatus disclosed herein relates in general to the cryopreservation of biological materials. More specifically, the present disclosure relates to a method and apparatus for cryopreservation of various cell types such as hematopoietic stem and progenitor cells, mesenchymal stem and progenitor cells and endothelial progenitor cells found in normal blood, placental-cord blood, bone marrow or the stromal vascular fraction cells resident in adipose tissue.

Description of the Related Art

Hematopoietic stem and progenitor cells make up a very small percentage of the nucleated cells normally found in bone marrow, cord blood or adipose tissue and are even rarer in normal blood. For instance, only approximately one in five hundred bone marrow cells are nucleated cells, and only one in one thousand nucleated bone marrow cells is a progenitor cell; and stem cells occur at an even lower frequency.

Reconstitution of the hematopoietic system for patients in need has conventionally been accomplished by transfusion into a patient of hematopoietic stem and progenitor cells from the bone marrow or cord blood of suitable Human Leukocyte Antigen (HLA) matched donors. These donor stem and progenitor cells migrate to the interior of bones, take up residence, and then typically multiply and replace the blood cells responsible for protective immunity, tissue repair, clotting, oxygen transport and other functions of the patient's blood. In a successful transplant treatment, the blood, bone marrow, spleen, thymus, and other organs of immunity are repopulated with cells derived from the donor.

These types of transplants have been used with increasing success to treat various fatal or crippling diseases, including certain types of anemia such as aplastic anemia, immune deficiencies, cancers such as lymphoma or leukemia, carcinomas, various solid tumors, genetic disorders of hematopoiesis and inherited storage diseases. Improvements in hematopoietic reconstitution techniques are thus greatly needed.

It is known that hematopoietic reconstitution is best accomplished when the donor is a perfectly matched (genetically identical) sibling. But often a sibling donor is either not a perfect match, or is unwilling or unavailable to donate. Realistically, most often the best available match is from cord blood or bone marrow from an unrelated donor that is acceptably matched. Moreover, when stem cells are provided to the patient, the patient is often near death and needs these cells inserted so that the patient can begin producing their own blood and their own immune system. There is a real chance for death if there is an insufficient number of cells or if the inserted stem cells are not completely sterile. This is because often these patients have been ablated and their immune system completely killed off, so even the slightest infection can be fatal. The end goal is that eventually the new cells inserted will establish a new immune system for the patient. To increase the likelihood of the immediate availability of an acceptable match, a large registry of potential bone marrow donors is maintained and a large cryopreserved inventory of cord blood donor stem and progenitor cells is maintained in a sterile condition to be made available for any patient in need. Blood substitution and blood supply is a permanent strategic and logistical problem of medical services around the world because blood, which is a biological drug, has a limited shelf life and requires special transport and stringent conditions of use. This is especially true with cord blood, and as a result, this source of stem and progenitor cells is typically in a frozen state so they may be collected and stored long before use.

Long term storage of blood cells and other living cells after they have been removed or separated from a donating organism has long been accomplished through freezing. The cryopreservation and recovery of such cells, however, has proven to be quite troublesome. Simple physics dictates that the cells are subjected to relatively harsh conditions during both the freezing and thawing cycles involved in cryopreservation, often resulting in a low survivability rate. The destruction of the cells occurs as the external medium freezes and the cells attempt to maintain equilibrium, thereby losing water and ultimately increasing intracellular solute concentration until intracellular freezing occurs at temperatures below 0 degrees C.

Substantial time and effort has been expended in an effort to maximize the viability of thawed cells, yet there are no known approaches that adequately solve the problem and provide an automatic record of cell survivability. Such efforts have generally focused on the development of cryoprotective agents, the insertion of said cryoprotective agents into the cell solution, and the establishment of optimal cooling and warming rates.

Protection of cells from freezing is achieved by adding so-called cryoprotective agents. Since these cryoprotectants usually cause a significant increase in osmolality, it is nevertheless necessary to have all the procedures monitored, and to have osmotic changes under control to avoid irreversible damage to cellular structures and membranes. Cryoprotection by solute addition of a cryoprotective agent occurs through two mechanisms. The first is intracellular; wherein the amount of ice formed within the cell is reduced throughout the process. The second is extracellular, wherein water flow out of the cell decreases in response to a decreased vapor pressure caused by the formation of ice in the solute surrounding the cells.

Dimethyl sulfoxide (DMSO) is the most commonly used cryoprotectant for mononuclear cells, including the hematopoietic and mesenchymal stem and progenitor cells resident in umbilical cord blood, bone marrow, and adipose derived stromal vascular fraction cells. DMSO is an organosulfur compound having the formula $(CH_3)_2SO$. When added to cell media, DMSO reduces ice formation and thereby maximizes cell viability during the freezing and thawing process.

However, the introduction of DMSO to these cell solutions is accompanied by a substantial downside, specifically the exothermic release of heat inherent as DMSO and $H_2O$ mix. This heat may be of an intensity sufficient to kill the cells if not strictly controlled. Furthermore, DMSO is a powerful solvent that should minimally contact cells directly when in high concentrations. Providing a means of assuring the sterility of the cell solution while adding the DMSO, controlling the rate of introduction of the DMSO solution and assuring its rapid, homogenous distribution within the cell solution is thus both critical and difficult. Moreover, it is very desirable that the cell solution is properly mixed with the DMSO solution by eliminating formation of hot spots and standing waves. Because of these risks, historically a clinician carefully and by syringe pumped or by hand, introduced DMSO solution into a cell solution sample that was sandwiched between ice packs to absorb the exothermic heat. While these methods can be successful for a skilled clinician, they leave too much room for error. Automated record keeping of the mixing process and fluid temperatures is traditionally not present.

Because of the above it is, unfortunately, not uncommon to discover low viability of cells after thawing. When this occurs, it is often not known at which stage in the entire cell processing workflow the failure occurred. There is thus a need to more carefully monitor both the precise mixing of the DMSO and the cell solution and the temperature of the cell solution during and after the introduction of DMSO to that cell solution.

Often it is necessary to provide a patient with multiple dosing from a single donor sample. For this to occur, there is a need to separate the donor cell solution into multiple portions, each in their own hermetically sealed container and each container joined to the other containers to ensure the identity and common controlled freezing rate of each compartment for quality control. Further, while stored at cryogenic temperatures, each hermetically sealed container must also be able to be separated and retrieved from the other joined containers, without piercing the hermetic seal of any of the containers, allowing each container to be thawed separately from the others.

One existing cryopreservation method describes isolating and cryopreserving of human white cells from whole blood. The sequence of operations leading to the separation of red cells, white cells, platelets and plasma is presented in a flow diagram of a bag system for the cryopreservation of leukocytes. Freezing of the white cells is accomplished by the introduction of a combination of hydroxyethyl starch (HES), which functions as both a sedimenting agent and a cryoprotective agent, DMSO. A preferred combination is 4% HES with 5% DMSO. White cell separation is interfaced with collection methods for plasma and platelets so as to conserve all major cell types. However, such a method does not include a means to pump a cryoprotectant solution to the cell solution in a slow, calculated and monitored rate under completely sterile conditions. Moreover, this method does not allow the nutation mixing of the contents of the cell solution and mixing of cell solution with a cryoprotectant solution by eliminating standing waves formed during the mixing processes.

Another existing method describes cryopreservation of peripheral blood lymphocytes. This method comprising the steps of: freezing cells and a cryopreservation medium wherein the cells are freshly isolated lymphocytes, hematopoietic stem cells, lymphocytes which are modified ex vivo, or a combination thereof, wherein the medium does not comprise DMSO or serum, and wherein the arabinogalactan in the medium results in a high post-thaw survival rate for the freshly isolated cells which are modified ex vivo. However, this method does not allow the nutation mixing of the contents of the cell solution, or the mixing of cell solution with a cryoprotectant solution by eliminating standing waves formed during the nutation mixing processes. In addition, this method does not ensure all cells in the cell solution within a container remain in the cell solution and do not attach to the internal surface of the container.

Yet another existing auto-nucleating cryopreservation device includes a tube containing a crystalline cholesterol matrix. The ends of the tube are closed by a membrane that is impermeable to the cholesterol but permeable to liquids contained in a cryopreservation vessel. The auto-nucleating device provides a site for ice nucleation during freezing of the liquid within the vessel. One such cryopreservation vessel is a flexible vial having a closed port at one end adapted to be pierced by a needle to withdraw the liquid within, and an opposite end that is initially open to receive the liquid. Another vessel includes an adaptor mounted to liquid container with a tubular branch closed by a needle septum, and the other tubular branch provided with a barbed fitting for engaging a flexible tube that terminates in the needle septum. In another embodiment, the vessel includes an inlet and vent branch at the top of the container and an outlet septum at a bottom opening. However, this device does not allow nutation mixing of the contents of the cell solution and the mixing of the cell solution with a cryoprotectant solution under sterile conditions by eliminating standing waves formed during the nutation mixing process. Moreover, the device cannot regulate, maintain, and record temperature of the mixture of the cell solution and the cryoprotectant solution before, during and after the cryoprotectant solution insertion.

Various other cryopreservation devices and methods currently available do not include a means to regulate temperature of the cell solution within a mixing container by conduction due to direct heat transfer. Finally, U.S. Pat. No. 8,747,289 B2 (application Ser. No. 13/634520, filed by the Applicant on Mar. 17, 2011 and claiming priority to U.S. Provisional app. 61/315109 filed Mar. 18, 2010 and U.S. Provisional app. 61/436964 filed Jan. 27, 2011) describes an apparatus and method for purifying and harvesting certain cell populations in blood or bone marrow by depleting at least one of red blood cells, granulocytes, or platelets from a sample comprising blood, bone marrow, or stromal vascular fraction cells separated from adipose tissue. The apparatus provides the capture of and means for increasing the concentration of certain cell types. The apparatus comprises a sterile, single use rigid, self-supporting cartridge within which the automated depletion, purification and harvesting of target cell populations occurs and all components may be distributed. FIG. 4 illustrates an example of a prior art rigid disposable cartridge within which the certain cell types are concentrated. The rigid disposable cartridge 150 is cylindrical, single-use, and constructed preferably of hard plastic, and more preferably optically clear polycarbonate. The rigid disposable cartridge 150 includes an output tubing 152 that can be connected to at least one tubing to provide for a transfer of materials from the rigid disposable cartridge 150. A top portion of the disposable cartridge includes a 0.2-micron filter 154 to provide passage for displaced air from within the funnel when blood or bone marrow is introduced into the funnel. The control module 156 in which the disposable cartridge 150 is seated is a battery-operated, electro-mechanical device with optical and gravitational sensing. The preferred embodiment also comprises a membrane switch 158, a seven segment digital read out 160 and three light emitting diodes 162 to inform and assist the user. A universal battery indicator 164 alerts the user to the charge condition of the battery. Shown in the center is an on-off switch 166 for the control module and a Light Emitting Diode (LED) 162, and on the right is the seven segment digital read out 160 and the LED 162 that indicates whether the cell harvest run was performed as designed and, if not, which error in operation may have occurred. Although the apparatus and related method of use are highly useful, such a method does not include a means that cryopreserves the collected cells.

There is thus a need for a simple, universal processing set that provides an optimum environment for cryoprotecting a clinically relevant population of stem and progenitor cells, while maintaining the sterility and viability of the cells and facilitating their long-term storage at cryogenic temperatures. Such an apparatus and method would include individual sealed containers, each containing a portion of the original volume of collected bone marrow or cord blood containing essentially all the nucleated cells, and be individually cryoprotected and frozen in a manner that assures a high degree of post-thaw cell viability. Such an apparatus and method would include a means to pump a cryoprotectant solution to the cell solution in a slow, calculated and monitored rate under completely sterile conditions. Such an apparatus would preferably include a container that is configured to allow the nutation mixing of the contents of the cell solution and mixing of the cell solution with a cryoprotectant solution by eliminating standing waves formed during the mixing processes. Such an apparatus and method would ensure all cells resident in a cell solution within a container are contained in the cell solution and do not adhere to the internal surface of the container. Such a system would include a means to regulate the temperature of the cell solution within a mixing container by conduction due to direct heat transfer. This apparatus would be configured to communicate with a storage server so as to transmit data gathered during the method for cryopreservation of biological materials. Furthermore, such an apparatus and method would include the container that optimizes the rate of dissemination of DMSO so that the DMSO is quickly and homogenously diffused, consequently reducing incidents of cell death. Further, this apparatus and method would provide a workstation in which the temperature of the mixture of the harvested cell solution and the cryoprotectant solution before, during and after cryoprotectant solution insertion is regulated, maintained and recorded.

SUMMARY OF THE DISCLOSURE

To minimize the limitations found in the prior art, and to minimize other limitations that will be apparent upon the reading of the specification, the preferred embodiment of the present invention provides an apparatus and related method for optimizing the cryopreservation of various types of cells, including but not limited to hematopoietic and mesenchymal stem and progenitor cells, and endothelial progenitor cells found in normal blood, placental/cord blood, bone marrow or the stromal vascular fraction of adipose tissue.

The apparatus and related method provide for the precise, temperature controlled, homogenously distributed introduction of a cryoprotectant containing dimethyl sulfoxide (DMSO) into a solution containing nucleated cells in a manner that provides a safe increase in osmotic pressure and a controlled release of exothermic heat within the cells as the DMSO penetrates the cell membrane and replaces water molecules prior to the freezing of the cells. The apparatus and described method of use facilitate the sterile transfer of cells from a prior art volume reduction process to at least one freezing container. In this process, a single cryoprotectant mixing chamber is described that optimizes the rate of dissemination of DMSO so that said DMSO is quickly and homogenously diffused, consequently reducing incidents of cell death.

The apparatus comprises a cryopreservation workstation, a rigid disposable cartridge, and a freezing bag assembly. The cryopreservation workstation comprises an upper platform, an upper mixing chamber holder, a freezing bag holder, a mixing module having a mixing module cap, a cooling plate and a mixing module door, a freezing bag air expresser, a cryoprotectant mixing chamber holder connected to the freezing bag air expresser, a syringe pump module having a syringe holder, an actuator plunger, a pair of retaining pins and a syringe pump module door. The rigid disposable cartridge is removably positioned on the upper platform and configured to harvest a cell solution.

The freezing bag assembly comprises a cryoprotectant mixing chamber having a cryoprotectant filter with a detachable filter cap, at least one input tubing assembly attached to the cryoprotectant mixing chamber, at least one luer lock fitting attached to a distal end of the at least one input tubing assembly, at least one sampling site attached to the at least one input tubing assembly, at least one air filter attached to the at least one input tubing assembly, at least one sampling bulb attached to the at least one input tubing assembly, a Y connector tubing attached to the cryoprotectant mixing chamber, at least one three dimensional freezing bag attached to the Y connector tubing, and at least one spike port attached to the at least one freezing bag.

In one embodiment, a method for cryopreservation of biological materials in a sterile environment is described. The rigid disposable cartridge having harvested cell solution is heat sealed the at least one input tubing assembly of the freezing bag assembly. The rigid disposable cartridge is placed on the upper platform utilizing at least one locking means and the cryoprotectant mixing chamber is placed in the cryoprotectant mixing chamber holder. The filter cap is removed from the cryoprotectant filter on the cryoprotectant mixing chamber and a power button is pressed on the cryopreservation workstation to repeatedly tilt the upper platform placed with the rigid disposable cartridge to the left and right with a rocking motion on an axis relative to the upper platform.

The slide clamp or hemostat on the at least one input tubing assembly is released for allowing the transfer of the harvested cell solution to the cryoprotectant mixing chamber through the at least one input tubing assembly from the rigid disposable cartridge. After the harvested cell solution is passed to the cryoprotectant mixing chamber from the rigid disposable cartridge, the at least one input tubing assembly is sealed utilizing the slide clamp or hemostat and the freezing bag assembly is removed from the rigid disposable cartridge.

The cryoprotectant mixing chamber is removed from the cryoprotectant mixing chamber holder and placed in the mixing module. The mixing module is nutated to mix the harvested cell solution contained in the cryoprotectant mixing chamber. The cryoprotectant mixing chamber is preferably three-sided and triangular shaped in nature, and the mixing occurs in three dimensions so as to avoid standing waves formed during nutating mixing of the contents of the cell solution. The harvested cell solution contained in the cryoprotectant mixing chamber is cooled utilizing the cooling plate in the mixing module. The freezing bag is inserted in the freezing bag air expresser and pressed to drive out air from the freezing bag.

The syringe pump module door is opened by pushing on the door and activating a spring loaded latch. A syringe filled with a cryoprotectant solution is placed in the syringe holder. The filter cap is removed from the cryoprotectant filter and a distal end of a syringe extension tubing attached at a tip portion of the syringe is connected to the cryoprotectant filter. The syringe is actuated via the actuator plunger to dispense the cryoprotectant solution to the cryoprotectant mixing chamber through the syringe extension tubing. The cryoprotectant solution and the harvested cell solution in the cryoprotectant mixing chamber are homogenously mixed by titling the mixing module. The mixture of cryoprotectant solution with the harvested cell solution contained in the cryoprotectant mixing chamber is cooled utilizing the cooling plate in the mixing module.

The Y connector tubing between the freezing bag and the cryoprotectant mixing chamber is sealed using the slide clamp or hemostat. A handle on the freezing bag air expresser is rotated counter clockwise so as to substantially completely compress the freezing bag. The cryoprotectant mixing chamber is removed from the mixing module and simultaneously the freezing bag is removed from the freezing bag air expresser. The cryoprotectant mixing chamber is placed in the upper mixing chamber holder wherein the cryoprotectant filter is maintained in an uppermost position and the at least one air filter is placed into a filter hook.

The freezing bag is placed in the freezing bag holder. The slide clamp or hemostat on the Y connector tubing is removed thereby allowing cryoprotected cell solution to flow from the cryoprotectant mixing chamber into the freezing bag. Finally, the slide clamp or hemostat is placed above the Y connector tubing upstream from the Y connector tubing once cryoprotected cell solution flowing to the freezing bag ceases.

In another embodiment, the method further comprises the steps of rotating the cryoprotectant mixing chamber holder, with the cryoprotectant mixing chamber, clockwise until the cryoprotectant mixing chamber holder is pivoted to a vertical position, holding the sampling bulb such that the at least one input tubing assembly is maintained in an upright position, squeezing and releasing the sampling bulb to mix and obtain a representative pre-sample of the harvested cell solution, and sealing a sampling bulb tubing and removing the sampling bulb for confirmatory cell counts. The at least one input tubing assembly allows an operator to obtain the sample of the harvested cell solution yet not disrupt the sterile integrity of the harvested cell solution.

The apparatus and associated method provide, among other features, a means of sterile passage of the cell solution from the prior art volume reduction process into the set that does not allow the solvent action of the DMSO; a means of controlled-rate addition of the DMSO solution into the set to combine with the cell solution; a means of substantially absorbing the exothermic heat generated by the mixing of DMSO and $H_2O$ before it causes a rise in cell solution temperature great enough to reduce cell viability; a means of homogenous distribution of the DMSO throughout all the clinical cell solution during the introduction of the DMSO; and a means of sterile passage of the cryoprotected cell solution to one or more sealable storage containers.

A first objective of the present invention is to provide a simple, universal processing set that provides an optimum environment for cryoprotecting a clinically relevant population of stem and progenitor cells, while maintaining the sterility and viability of the cells and facilitating their long-term storage at cryogenic temperatures.

A second objective of the present invention is to provide an apparatus and method that includes individual sealed containers, each containing a fraction of the original volume of collected bone marrow or cord blood containing essentially all the nucleated cells, be individually cryoprotected and frozen in a manner that assures post thaw cell viability.

A third objective of the present invention is to provide an apparatus and method that includes a means to pump a cryoprotectant solution to the cell solution in a slow, calculated and monitored rate under a completely sterile condition.

A fourth objective of the present invention is to provide an apparatus that includes a container that is configured to allow nutating mixing of the contents of the cell solution and mixing of the cell solution with a cryoprotectant solution by eliminating standing waves formed during the nutating mixing processes.

A fifth objective of the present invention is to provide a means to regulate temperature of the cell solution within a mixing container by conduction due to direct heat transfer.

A sixth objective of the present invention is to provide an apparatus that is configured to communicate with a storage server so as to transmit data gathered during the method for cryopreservation of biological materials.

A seventh objective of the present invention is to provide an apparatus and method that provides a workstation in which the temperature of the mixture of the harvested cell solution and the cryoprotectant solution before, during and after cryoprotectant solution insertion is substantially regulated, maintained and recorded.

These and other advantages and features of the present invention are described with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

The present invention is a method and apparatus for optimizing the cryopreservation of blood cells and various other cell types such as hematopoietic stem and progenitor cells, mesenchymal stem and progenitor cells and endothelial progenitor cells found in normal blood, placental/cord blood, bone marrow or the stromal vascular fraction cells resident in adipose tissue in a sterile environment. The apparatus comprises a cryopreservation workstation 100 (See FIG. 1), a rigid disposable cartridge 150 (See FIG. 4), and a freezing bag assembly 200 (See FIG. 5).

Figure 1:
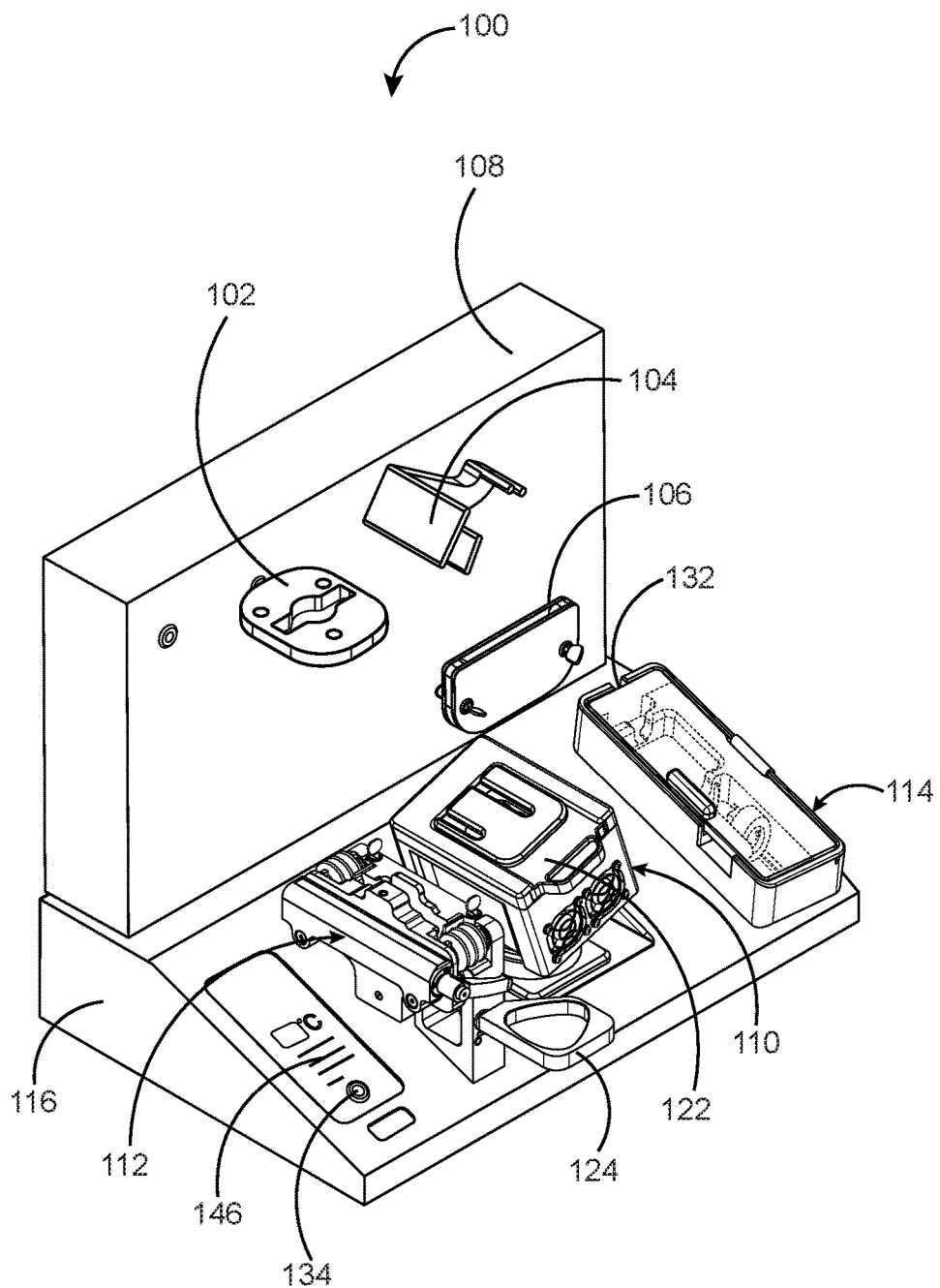
FIG. 1 illustrates a first perspective view of a cryopreservation work station in accordance with the preferred embodiment of the present invention.
Figure 2:
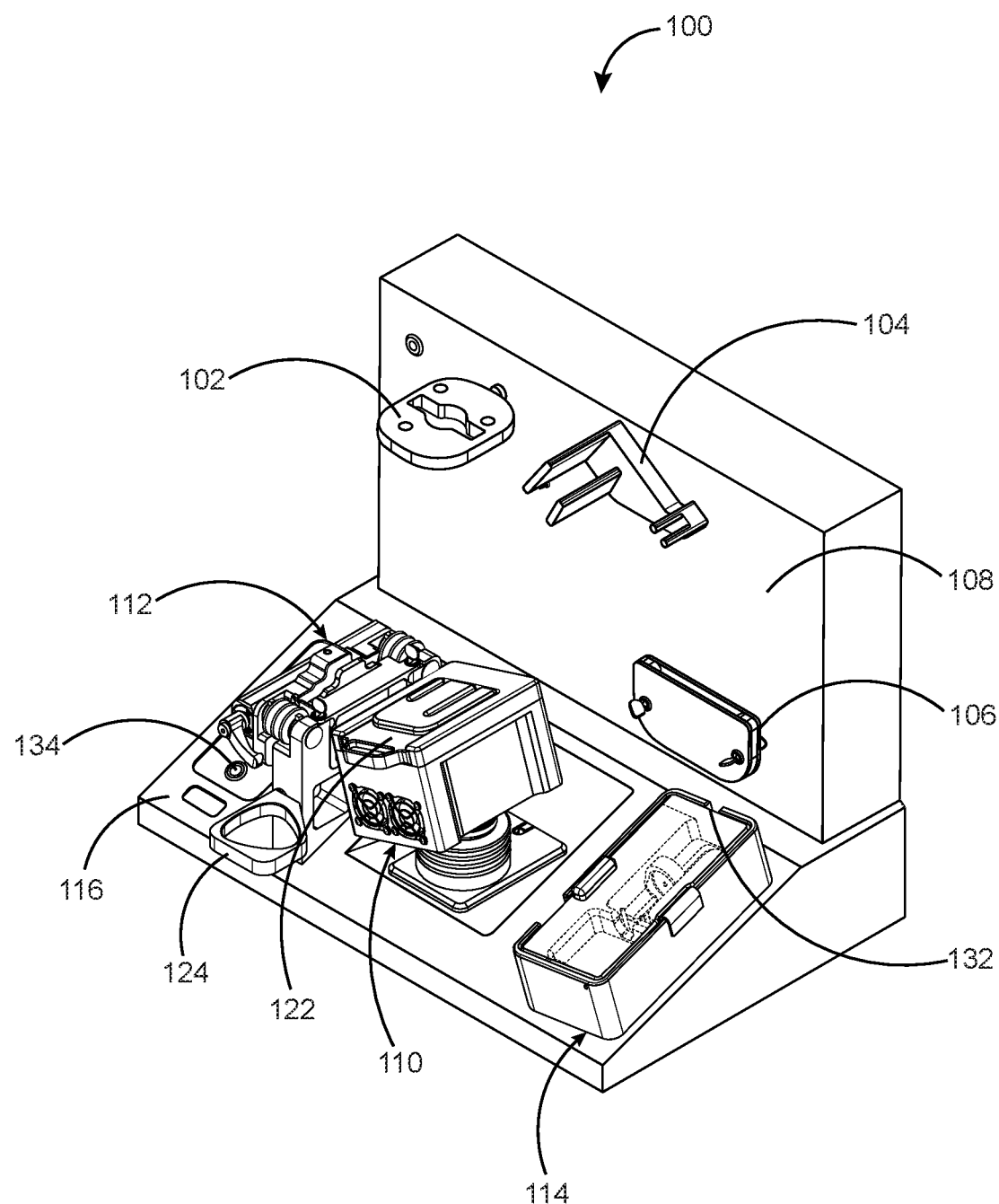
FIG. 2 illustrates a second perspective view of the cryopreservation work station in accordance with the preferred embodiment of the present invention.

Turning first to FIGS. 1 and 2, first and second perspective views of the cryopreservation work station 100 in accordance with the preferred embodiment of the present invention are illustrated. The cryopreservation workstation 100 comprises an upper platform 102, an upper mixing chamber holder 104 and a freezing bag holder 106, preferably all attached to an upper support member 108. The cryopreservation work station 100 further comprises a mixing module 110, a freezing bag air expresser 112, and a syringe pump module 114, which are placed in a plurality of compartments of a lower support member 116. The upper platform 102 includes at least one locking means 118 that is configured to hold the rigid disposable cartridge 150 (See FIG. 4). The locking means may be a plurality of locking tabs or any sort of fastener that allows a component inserted therein to click, snap, or latch into place. The mixing module 110 includes a mixing module cap 120 (See FIG. 12), a cooling plate (not shown) and a mixing module door 122. A cryoprotectant mixing chamber holder 124 is connected to the freezing bag air expresser 112. The syringe pump module 114 comprises a syringe holder 126 (See FIG. 20), an actuator plunger 128 (See FIG. 20), a pair of retaining pins 130 (See FIG. 20) and a syringe pump holder door 132.

Figure 4:
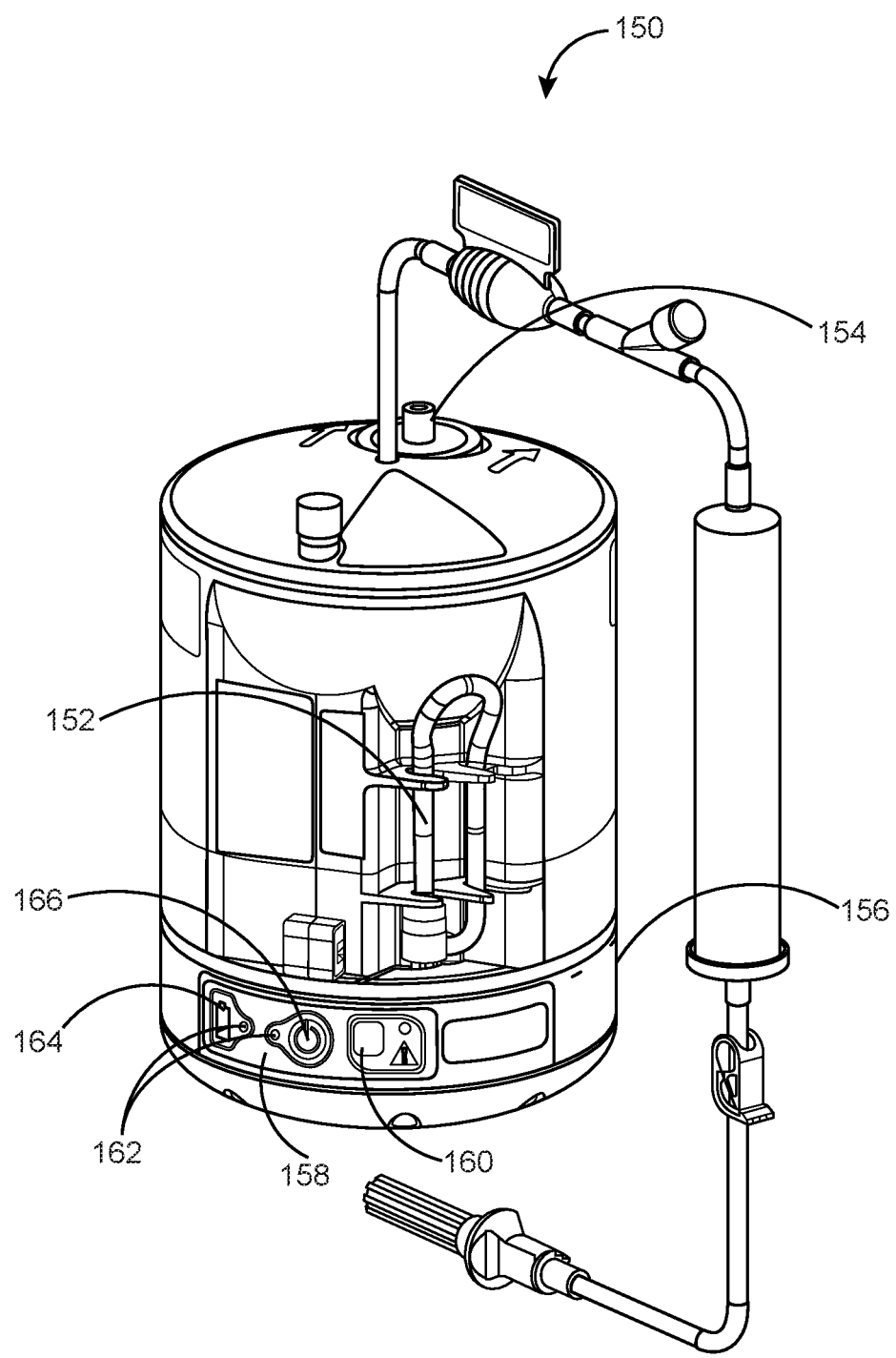
FIG. 4 illustrates an example of a prior art rigid disposable cartridge employed with a output tubing.
Figure 7:
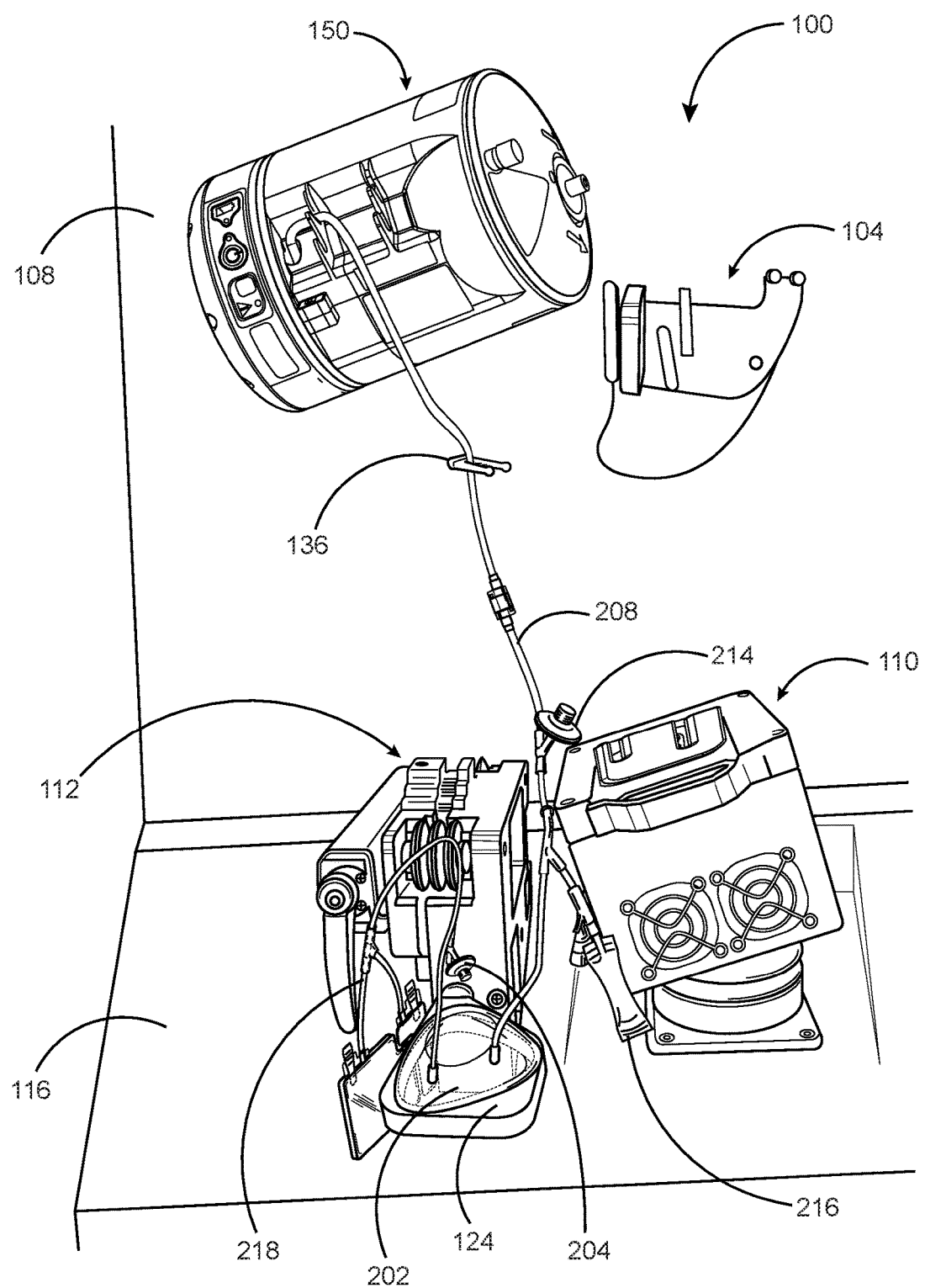
FIG. 7 illustrates a perspective view of the cryopreservation workstation in operation wherein the prior art rigid disposable cartridge is used therewith in a tilted position.
Figure 8:
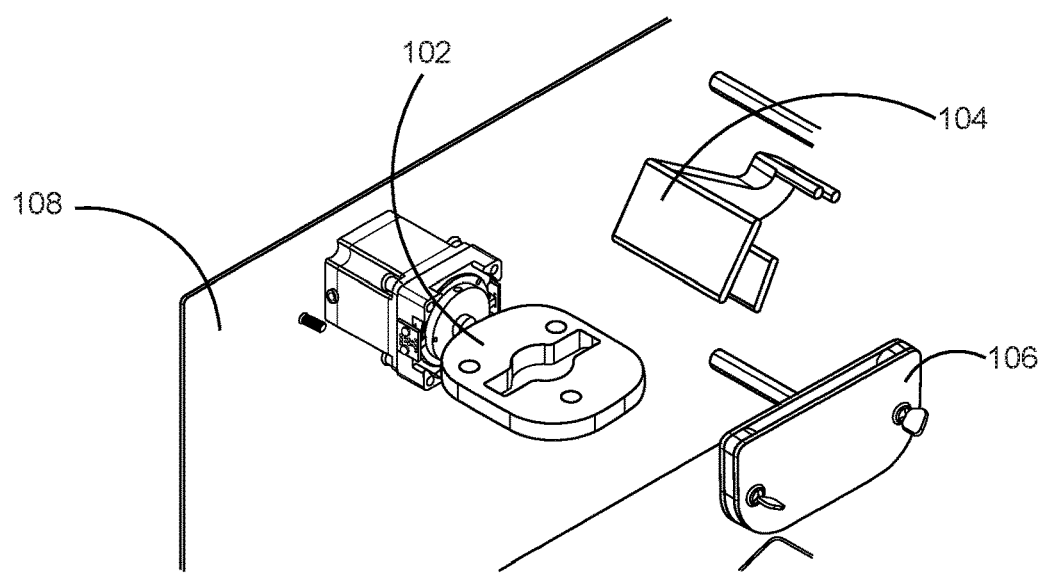
FIG. 8 illustrates a first enlarged partial perspective view of an upper platform, an upper mixing chamber holder and a freezing bag holder, as installed on an upper support member shown in FIG. 1.
Figure 9:
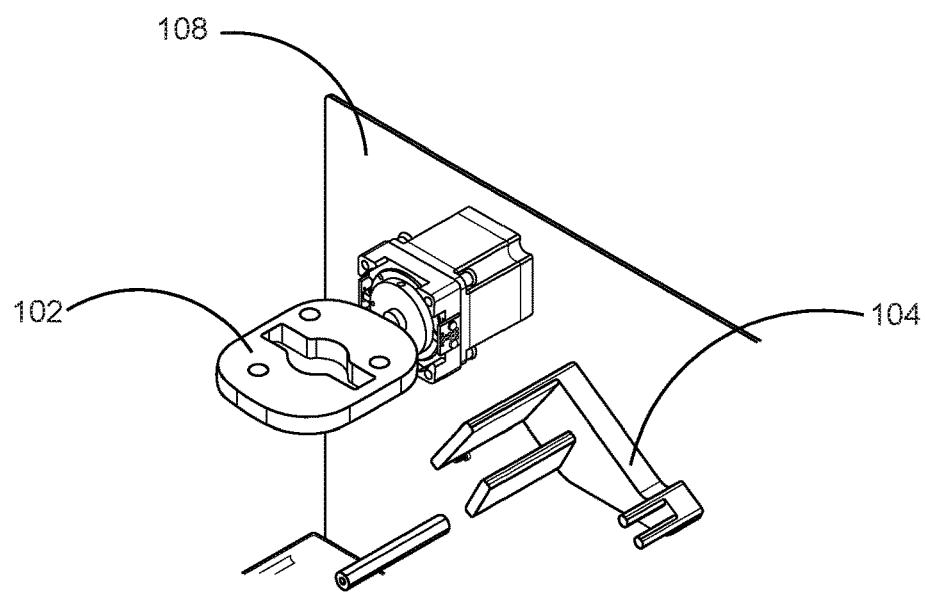
FIG. 9 illustrates a second enlarged partial perspective view of an upper platform, an upper mixing chamber holder and a freezing bag holder, as installed on an upper support member shown in FIG. 1.

In the preferred embodiment, the apparatus is configured to accept prior art disposable cartridge shown in FIG. 4 used in the volume reduction process described above and in more detail in U.S. Pat. No. 8,747,289 B2, granted Jun. 10, 2014, and which is incorporated herein by reference as if set out in full. The rigid disposable cartridge 150 within is removably positioned on the upper platform 102 of the cryopreservation workstation 100 as shown best in FIGS. 8 and 9. As a first step in the method, the rigid disposable cartridge 150 containing the harvested cell solution is placed on the upper platform 102 as shown in FIG. 7, such that an air filter 154 (See FIG. 4) is positioned to the left of an operator, preferably, at a 9 o'clock position when the rigid disposable cartridge 150 is viewed from above. Still other configurations are possible and the invention should not be limited to those described herein. Preferably, the operator squeezes the at least one locking means 118 on the upper platform 102 so as to place the rigid disposable cartridge 150 onto said upper platform 102. After placing the rigid disposable cartridge 150 onto the upper platform 102, the operator releases the at least one locking means 118 and ensures the rigid disposable cartridge 150 is locked in place. In some embodiments, additional containers of fluid are placed on the upper platform 102 so the fluid can be agitated to mix the fluid thoroughly within the containers.

Figure 5:
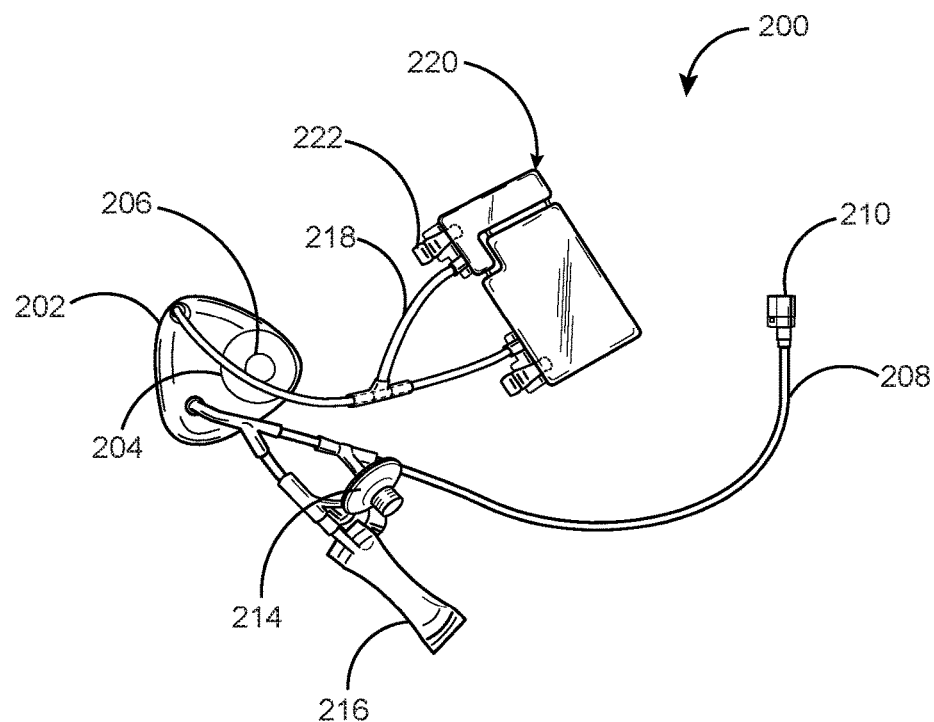
FIG. 5 illustrates a perspective view of a freezing bag assembly in accordance with the preferred embodiment of the present invention.

Referring to FIG. 5, a perspective view of a freezing bag assembly 200 in accordance with the preferred embodiment of the present invention is illustrated. Preferably, the rigid disposable cartridge 150 is heat sealed to the freezing bag assembly 200 prior to placing on the upper platform 102. The freezing bag assembly 200 comprises a cryoprotectant mixing chamber 202 having a cryoprotectant filter 204 with at least one detachable filter cap 206. The cryoprotectant filter 204 has a pore size of preferably 0.2 microns. The freezing bag assembly 200 further comprises at least one input tubing assembly 208 attached to the cryoprotectant mixing chamber 202, at least one luer lock fitting 210 attached to a distal end of the at least one input tubing assembly 208, at least one sampling site 212 attached to the at least one input tubing assembly 208, at least one air filter 214 attached to the at least one input tubing assembly 208, at least one sampling bulb 216 attached to the at least one input tubing assembly 208, at least one Y connector tubing 218 attached to the cryoprotectant mixing chamber 202, at least one three dimensional freezing bag 220 attached to the Y connector tubing 218, and at least one spike port 222 attached to the at least one freezing bag 220. Each freezing bag 220 includes integral aliquots such that a sample may be removed for confirmatory tests.

Preferably, the cryoprotectant filter 204 described herein is a Dimethyl sulfoxide (DMSO) filter and the cryoprotectant solution used is DMSO solution. The cryoprotectant filter 204 is insoluble to DMSO and remains undamaged as the DMSO passes through the cryoprotectant filter 204. Preferably, the cryoprotectant filter 204 is a nylon membrane, but other plastics may also be used, such as LDPE (low-density polyethylene), HDPE (high-density polyethylene), PP (polypropylene), PPCO (polypropylene copolymer), PMP (polymethylpentene), FEP (TEFLON® FEP (fluorinated ethylene propylene)) TFE (TEFLON® TFE (tetrafluoroethylene)) PF(TEFLON® PFA (polyfluoroalkoxy)), and FLPE (fluorinated polyethylene). All components of the freezing bag assembly 200 are initially contained within a sterile pouch to be opened prior to use. The cryoprotectant mixing chamber 202, the cryoprotectant filter 204, the Y connector tubing 218 and the freezing bag 220 are all durable to the solvent effects of cryoprotectant solution used for cryopreservation and the Y connector tubing 218 and the freezing bag 220 are durable to the cryogenic temperatures of Liquid Nitrogen. The surfaces of the freezing bag 220 and the sampling bulb 216 also may be adhered to by commercially available barcode adhesives.

Figure 6:
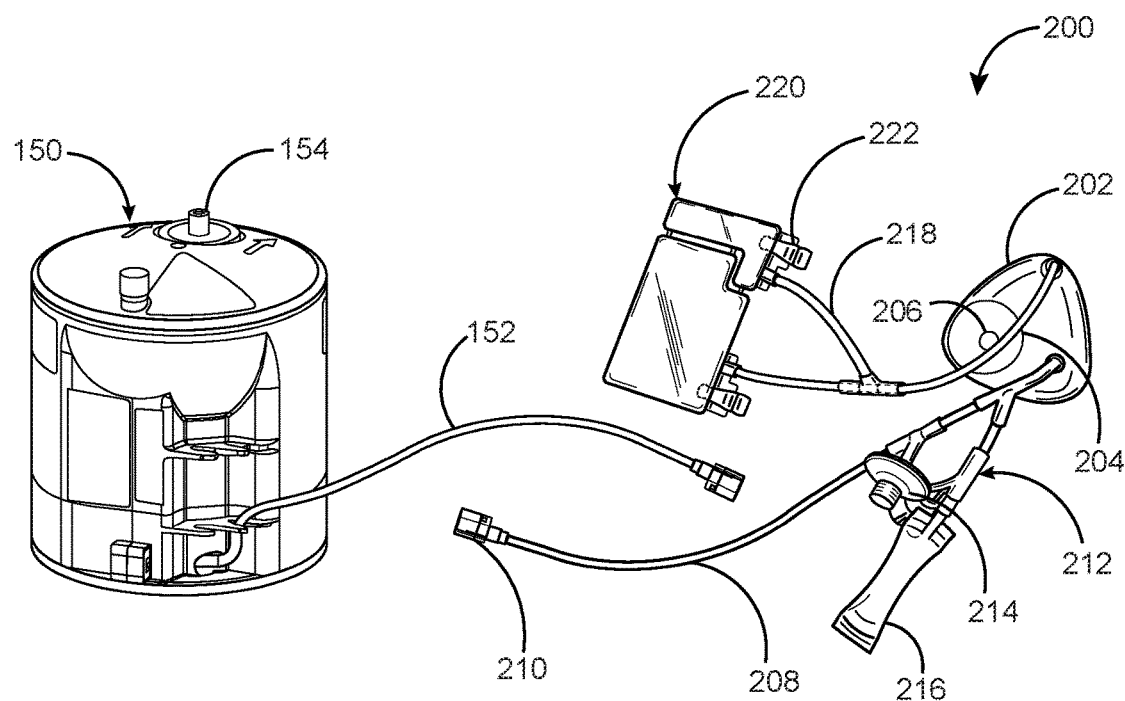
FIG. 6 illustrates a perspective view of the prior art rigid disposable cartridge and the freezing bag assembly prior to installation.

FIG. 6 shows the freezing bag assembly 200 prior to installation to the rigid disposable cartridge 150 and it is again shown as a step of the described method in association with the remainder of the apparatus in FIG. 7. The cryoprotectant mixing chamber 202 is connected sterilely to the rigid disposable cartridge 150 as shown in FIG. 7. The output tubing 152 of the rigid disposable cartridge 150 is heat sealed with the luer lock fitting 210 attached to the distal end of the at least one input tubing assembly 208 of the freezing bag assembly 200.

Figure 3:
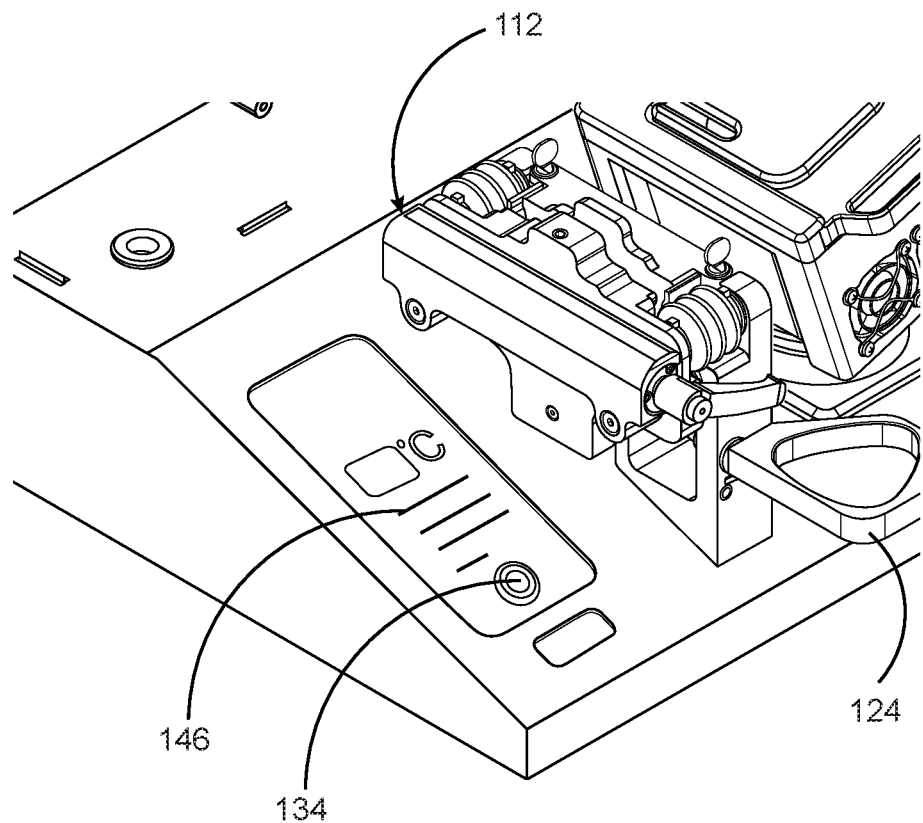
FIG. 3 illustrates an enlarged partial perspective view of the cryopreservation work station in accordance with the preferred embodiment of the present invention.

In the described method, after the rigid disposable cartridge 150 is placed on the upper platform 102, the cryoprotectant mixing chamber 202 is placed in the cryoprotectant mixing chamber holder 124, which is shown empty at the right side of FIG. 3 and is shown in FIG. 7 with the cryoprotectant mixing chamber 202 placed therein. The cryoprotectant mixing chamber 202 is preferably three-sided and triangular shaped in nature, and the mixing occurs in three dimensions so as to avoid standing waves formed during nutating mixing of the contents of the cell solution. Standing waves indicate mixing is not occurring and one could potentially have a high concentration of cryoprotectant solution that could be fatal to any cells it comes into contact with. The cryoprotectant mixing chamber 202 is positioned such that when viewed from above, the cryoprotectant filter 204 is facing away from the operator, preferably, at 12 o'clock position. Still other configurations are possible and should not be limited to those described herein. The operator then removes the filter cap 206 from the cryoprotectant filter 204 on the cryoprotectant mixing chamber 202 and then presses a workstation power button 134 shown best in the preferred embodiment in FIG. 3.

FIG. 7 illustrates a perspective view of the cryopreservation workstation 100 in operation after the workstation power button 134 has been pressed, wherein the rigid disposable cartridge 150 is used therewith in a tilted position. Here, the upper platform 102, and hence the rigid disposable cartridge 150, is repeatedly tilted left and right with a rocking motion on an axis relative to the upper platform 102. The upper platform 102 is shown in greater detail in FIGS. 8 and 9. During the rocking motion the upper platform 102, any object affixed thereto tilts approximately 20-50 degrees off center to the left and right as viewed from the front. In other embodiments, the tilting is multidirectional or circular and angles may include amounts less than 20 degrees and greater than 50 degrees. During, or immediately following this rocking motion of the rigid disposable cartridge 150, all cells resident in the cell solution within the rigid disposable cartridge 150 are contained in the cell solution and not adhering to the compartment wall.

A slide clamp or hemostat 136 preventing the fluid movement out of the rigid disposable cartridge 150 is released either automatically or via the actions of the operator, thereby allowing the first flow of harvested cell solution out of the rigid disposable cartridge 150. As explained in more detail in U.S. Pat. No. 8,747,289 B2, incorporated herein by reference, the first fluid is the buffy coat from the buffy coat harvest chamber, and it moves through the input tubing assembly 208 to the cryoprotectant mixing chamber 202. The flow of the harvested cell solution may be stopped at any time through manipulation of the slide clamp or hemostat 136 to re-pinch the input tubing assembly 208. If allowed to continue and as described in the aforementioned patent application, the harvested cell solution in the rigid disposable cartridge 150 is transferred to the cryoprotectant mixing chamber 202 and included in the cryopreservation process. The upper platform 102 continues its rocking motion for approximately one minute or sufficient time to allow substantially all the harvested cell solution and the suspended cells are transferred from the rigid disposable cartridge 150 to the cryoprotectant mixing chamber 202. The operator then seals the input tubing assembly 208 that connects the rigid disposable cartridge 150 and the freezing bag assembly 200 and removes the rigid disposable cartridge 150 from the freezing bag assembly 200.

Figure 10:
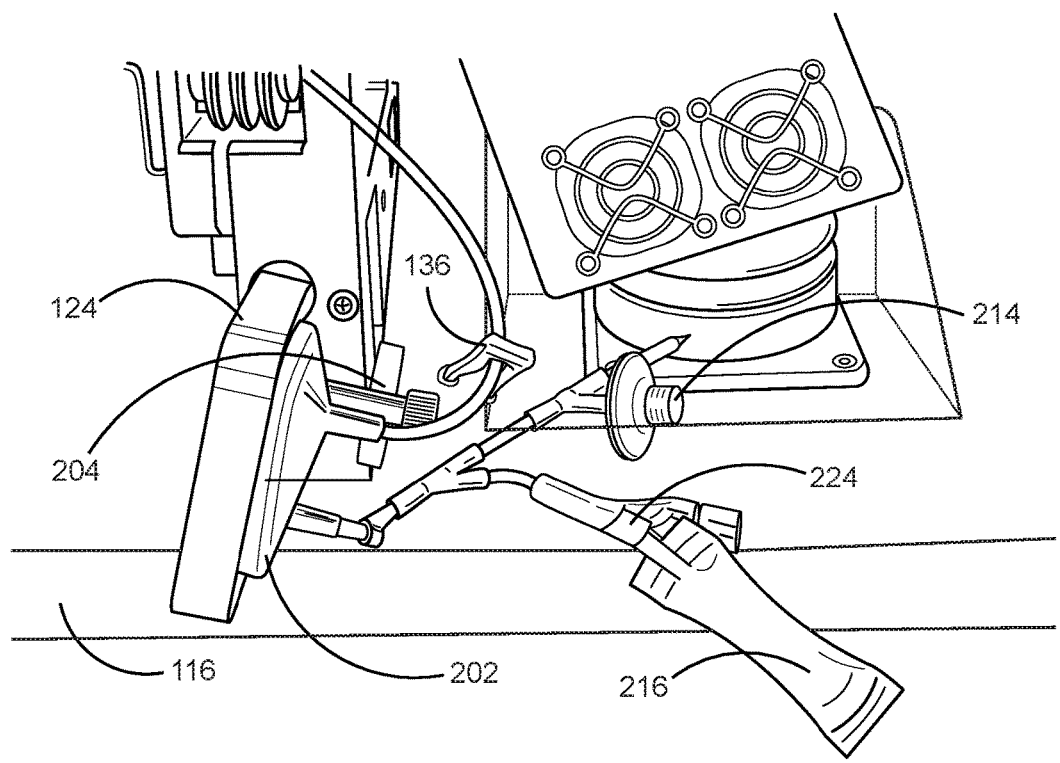
FIG. 10 illustrates a partial perspective view of a cryopreservation work station, illustrating a step wherein an operator squeezing and releasing a sampling bulb to mix and obtain a representative pre-sample of harvested cell solution.
Figure 11:
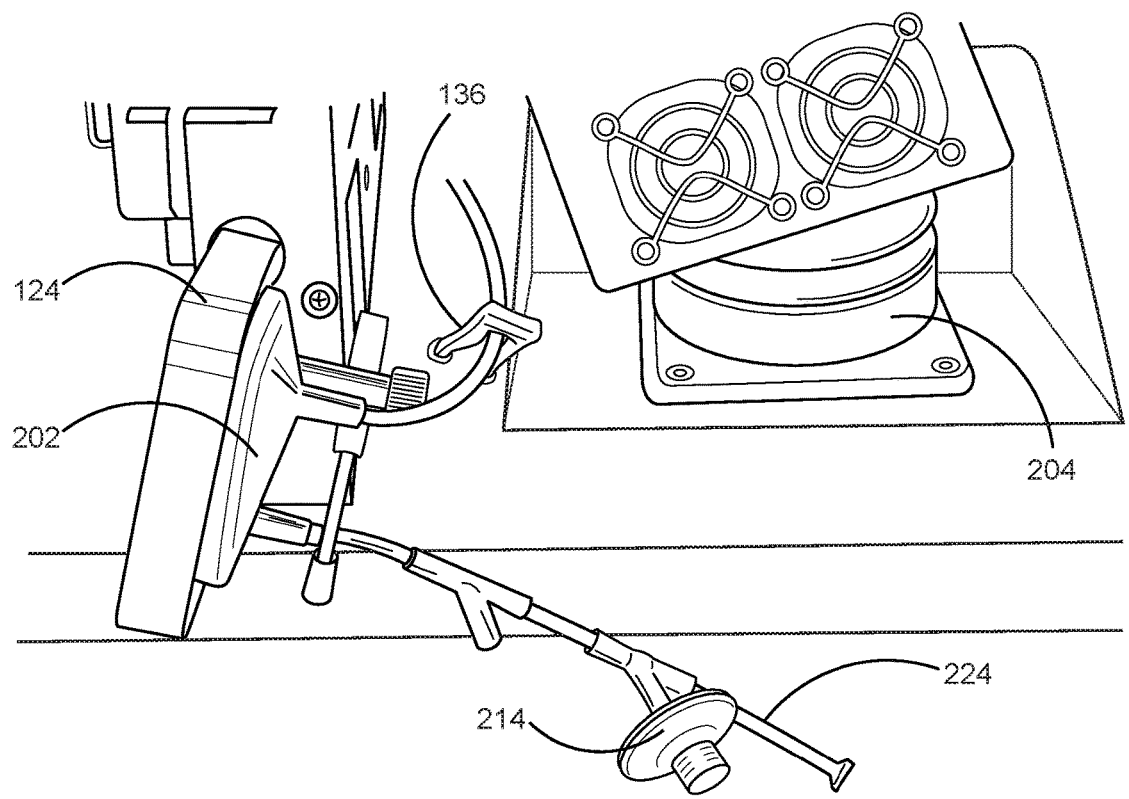
FIG. 11 illustrates a partial perspective view of a cryopreservation work station, wherein a sampling bulb tubing is sealed and the sampling bulb is removed.

FIG. 10 illustrates a partial perspective view of the cryopreservation work station 100, illustrating a step wherein a representative pre-sample of the harvested cell solution may optionally be obtained. The operator clamps the input tubing assembly 208 below the air filter 214 as close to the air filter 214 as possible using the slide clamp or hemostat 136 shown in FIG. 7. This action may also be automated. The operator then rotates the cryoprotectant mixing chamber holder 124, and hence the cryoprotectant mixing chamber 202, clockwise until it is pivoted in the near vertical position as shown in FIG. 10, and in contrast to the position shown in FIG. 7. The input tubing assembly 208 may then be sealed proximate the air filter 214 and detached from the freezing bag assembly 200 as shown in FIG. 10. A sample of the harvested cell solution collected by holding the sampling bulb 216 with the sampling bulb tubing 224 upright and then by squeezing the sampling bulb 216. Preferably, the sampling bulb 216 is squeezed and released approximately five times to mix and obtain a representative pre-sample of the harvested cell solution of anywhere from less than 1 ml to less than 10 ml. The at least one input tubing assembly 208 allows the operator to obtain the sample of the harvested cell solution in such a way that retains the sterile integrity of the harvested cell solution. If a sample is removed, next the sampling bulb tubing 224 is sealed and removed for confirmatory cell counts as shown in FIG. 11.

Figure 12:
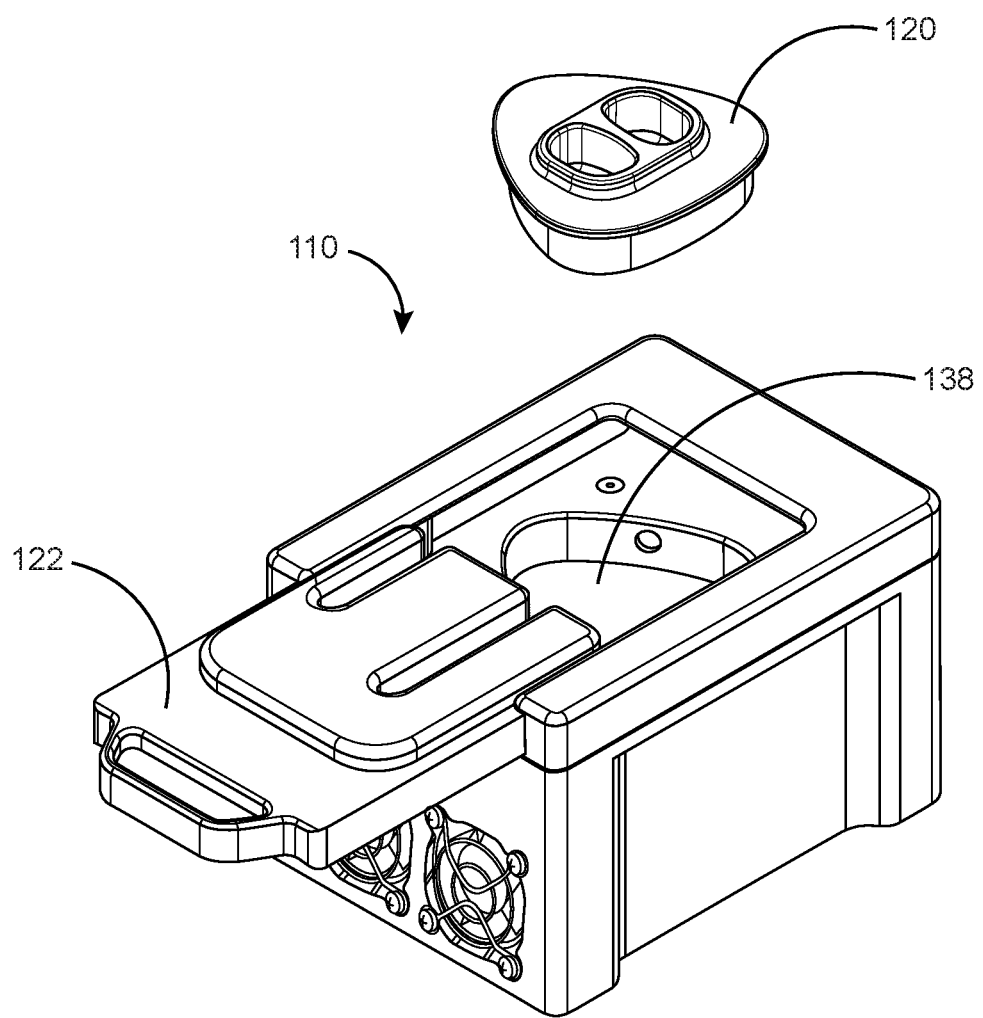
FIG. 12 illustrates a perspective view of a mixing module in an open configuration and a mixing module cap positioned apart and above from the mixing module.
Figure 17:
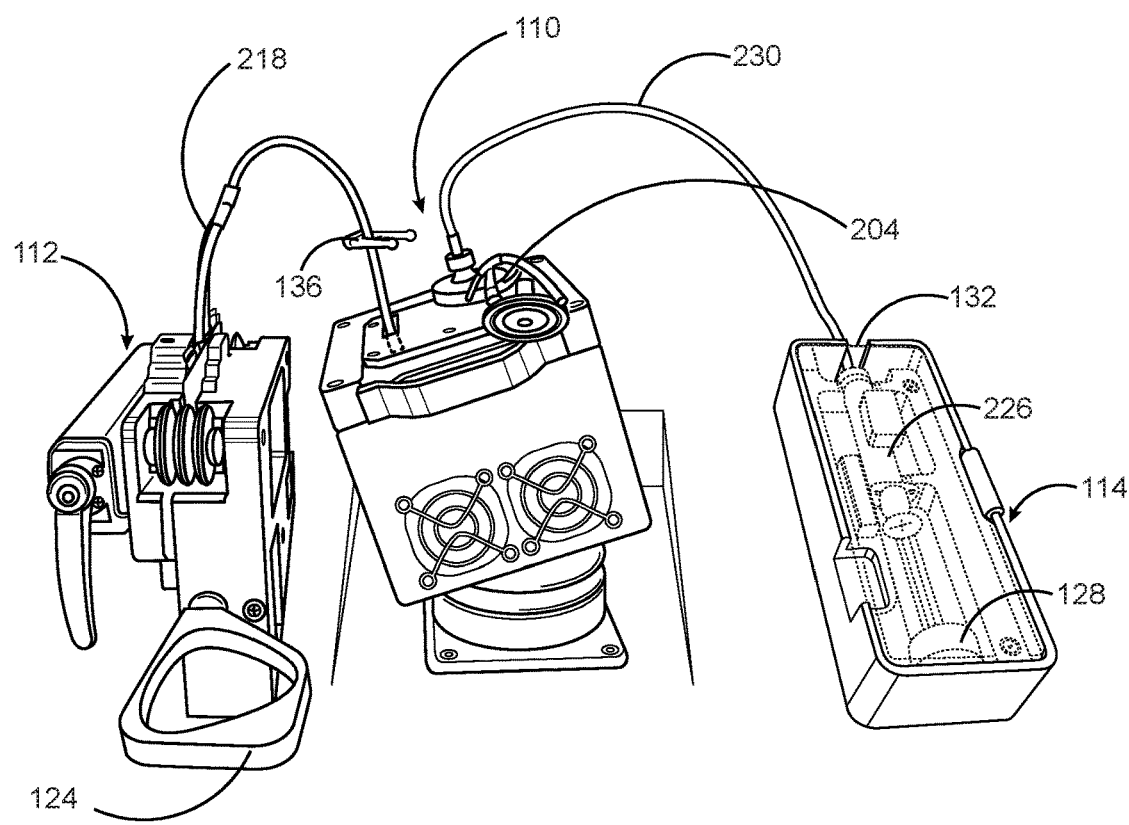
FIG. 17 illustrates the mixing module in operation with a cryoprotectant mixing chamber inserted therein, the freezing bag air expresser at left, and a syringe pump module at right in accordance with the preferred embodiment of the present invention.

Regardless as to whether a sample was removed as described above, next the cryoprotectant mixing chamber 202 is moved from the cryoprotectant mixing chamber holder 124 and placed in the mixing module 110 as shown empty in FIG. 12 and as shown with cryoprotectant mixing chamber 202 inserted therein in FIG. 17. In alternative embodiments the cryoprotectant mixing chamber holder 124 and the mixing module 110 may be the same component that combines the functions described herein in association with each separate component. Preferably, the mixing module 110 includes a mixing module cap 120 when the apparatus is not in use. This is shown best in FIG. 12 wherein the mixing module cap 120 is depicted above and apart from the remainder of the mixing module 110. In practice, the low temperature of the mixing module 110 is maintained when the mixing module cap 120 is placed thereon. If present, the mixing module cap 120 is removed as a part of this step.

Figure 13:
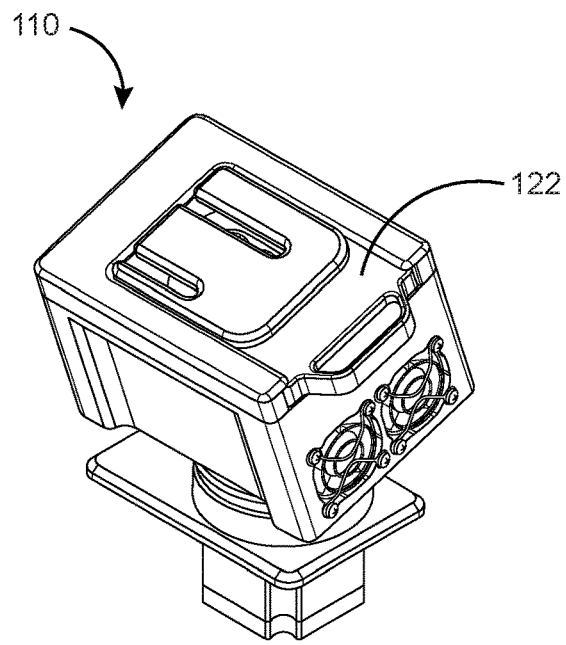
FIG. 13 illustrates a first perspective view of the mixing module wherein the mixing module is nutated approximately 20 degrees to the left.
Figure 14:
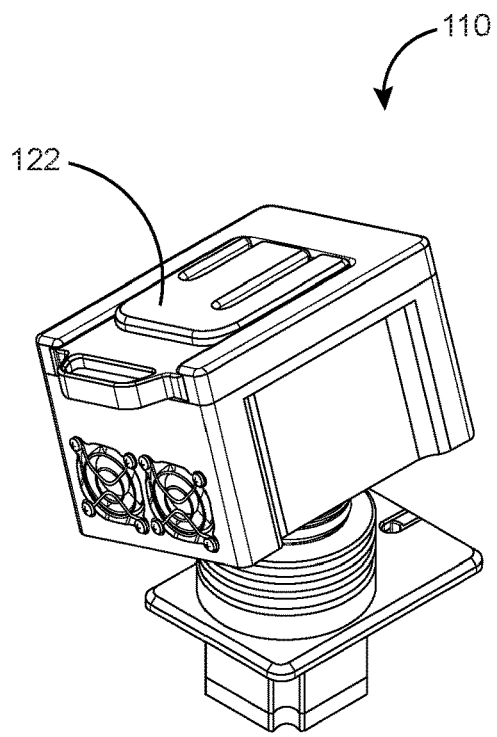
FIG. 14 illustrates a second perspective view of the mixing module, wherein the mixing module is nutated approximately 20 degrees to the left.

The mixing module 110 is preferably a nutating mixer comprising the cooling plate (not shown) that contacts a bottom surface of the cryoprotectant mixing chamber 202 when placed within the mixing module 110. The mixing module 110 is adapted to both cool and mix the harvested cell solution contained in the cryoprotectant mixing chamber 202. FIGS. 13 and 14 depict the mixing module 110 shown nutated approximately 20 degrees to the left as part of its orbital mixing process. Similarly, the mixing module 110 nutates toward the front, rear, and right, and may nutate in excess of 20 degrees or to a maximum less than 20 degrees. The angle of nutation may further be variable over time. The mixing module 110 contains the cooling plate (not shown) at the bottom of the depression 138 into which the cryoprotectant mixing chamber 202 is placed. The cryoprotectant mixing chamber 202 then comes into contact with the cooling plate (not shown) which is carefully temperature regulated, such that the temperature of the harvested cell solution within the cryoprotectant mixing chamber 202 is regulated by conduction due to direct heat transfer. The mixing module 110 preferably substantially maintains the temperature of the harvested cell solution within the cryoprotectant mixing chamber 202 as they are mixed in subsequent steps. The cryoprotectant mixing chamber 202 is oriented in the mixing module 110 such that the cryoprotectant filter 204 is facing away from the operator, preferably, at a 12 o'clock position when the cryoprotectant mixing chamber 202 is viewed from above. The mixing module 110 preferably comprises the mixing module door 122 on a top portion thereof, which substantially seals the cryoprotectant mixing chamber 202 inside the mixing module 110. As a part of this step, the mixing module door 122 is closed and locked while the cryoprotectant mixing chamber 202 is placed in the mixing module 110.

The cryoprotectant mixing chamber 202 is preferably triangular shaped when viewed from above, such that when the cryoprotectant mixing chamber 202 is rotated about on the mixing module 110, standing waves are eliminated. Further, the cryoprotectant mixing chamber 202 comprises air, which displaces water and further prevents formation of standing waves. The back and forth motion facilitates the rapid homogenous diffusion of the cryoprotectant solution.

Figure 15:
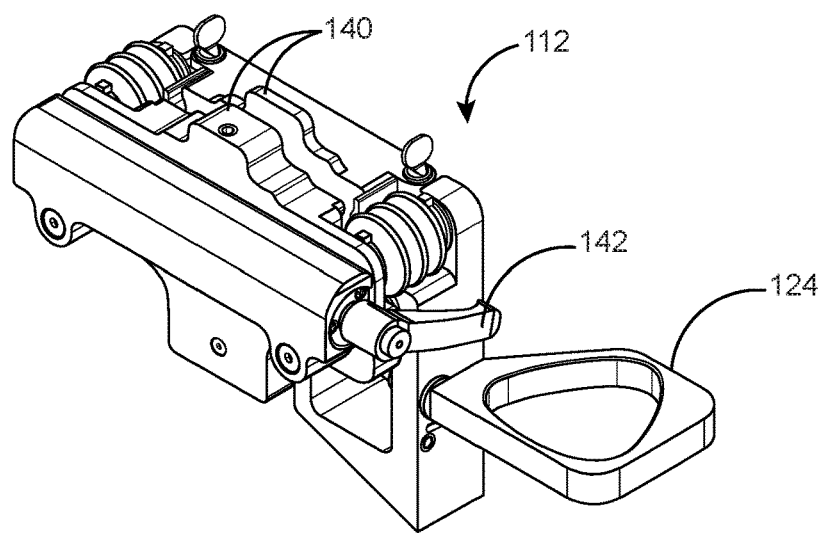
FIG. 15 illustrates a first perspective view of a freezing bag air expresser in accordance with the preferred embodiment of the present invention.
Figure 16:
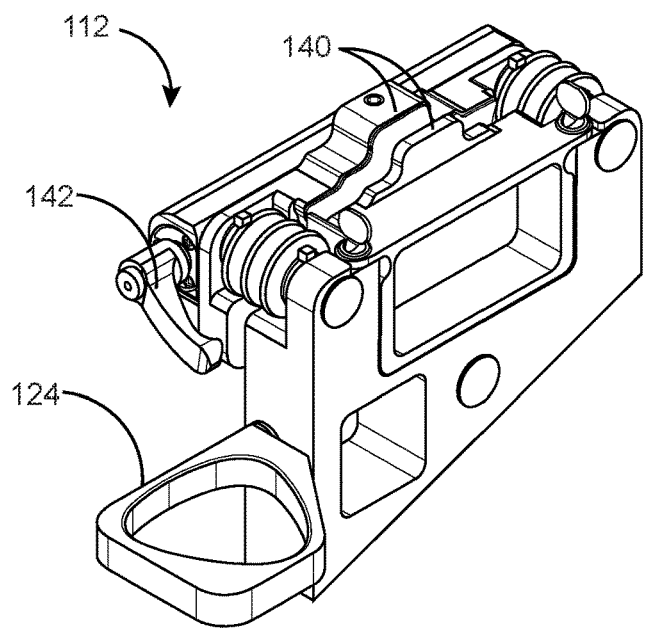
FIG. 16 illustrates a second perspective view of a freezing bag air expresser in accordance with the preferred embodiment of the present invention.

The freezing bag 220 is inserted in the freezing bag air expresser 112, which is shown best in FIGS. 15 and 16. The freezing bag 220 is inserted into the freezing bag air expresser 112 to drive out the air from the freezing bag 220 so that when the cryoprotected cell solution is transferred to the freezing bag 220 the inhalation of the bag 220 assists the fluid transfer. This step may occur before, after, or simultaneously with other steps. The freezing bag 220 is appressed between a pair of parallel walls 140 forming a clamp by rotating a handle 142 and the air is released out from the freezing bag 220 as shown best in FIG. 23. Other suitable methods can be used for expressing the air from the freezing bag 220, for example, rolling the bag 220 up from one end. The freezing bag assembly 200 is manufactured from plastic materials that are immune to the solvent action of the cryoprotectant solution (e.g. DMSO).

Figures 18, 19:
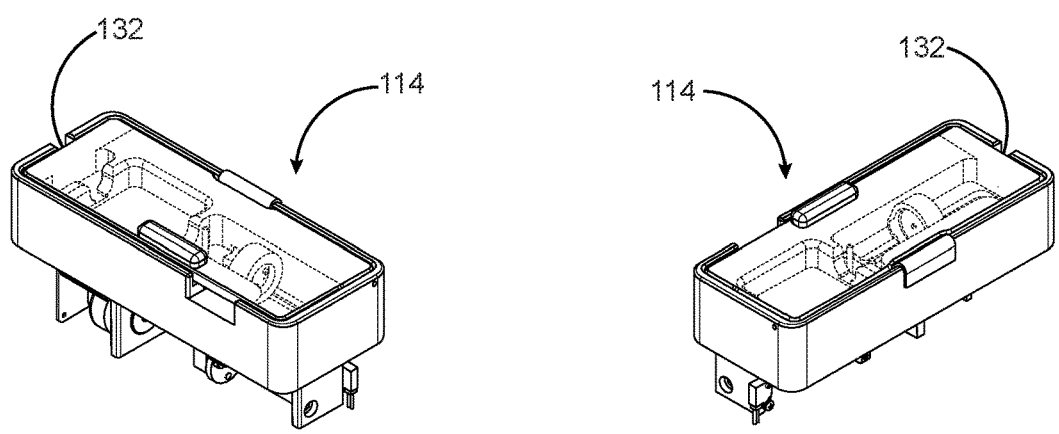
FIG. 18 illustrates a first perspective view of the syringe pump module wherein a syringe pump module door is transparent and in closed position.
FIG. 19 illustrates a second perspective view of the syringe pump module wherein a syringe pump module door is transparent and in closed position.
Figure 20:
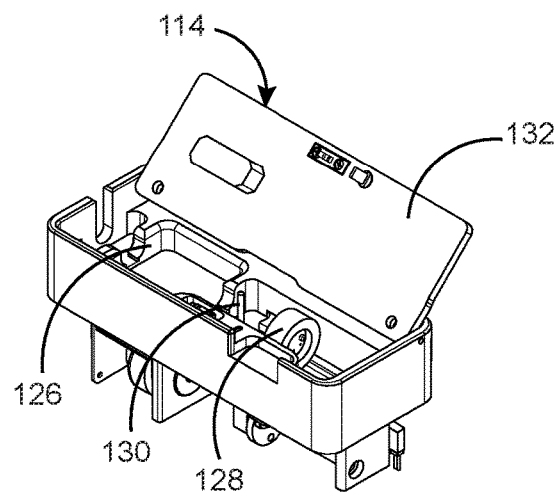
FIG. 20 illustrates a first perspective view of the syringe pump module wherein the syringe pump module door is in open position.
Figure 21:
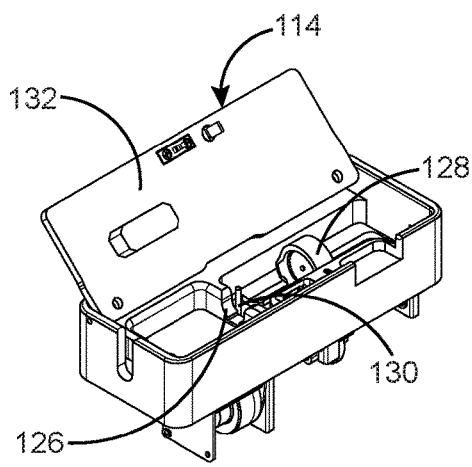
FIG. 21 illustrates a second perspective view of the syringe pump module wherein the syringe pump module door is in open position.
Figure 22:
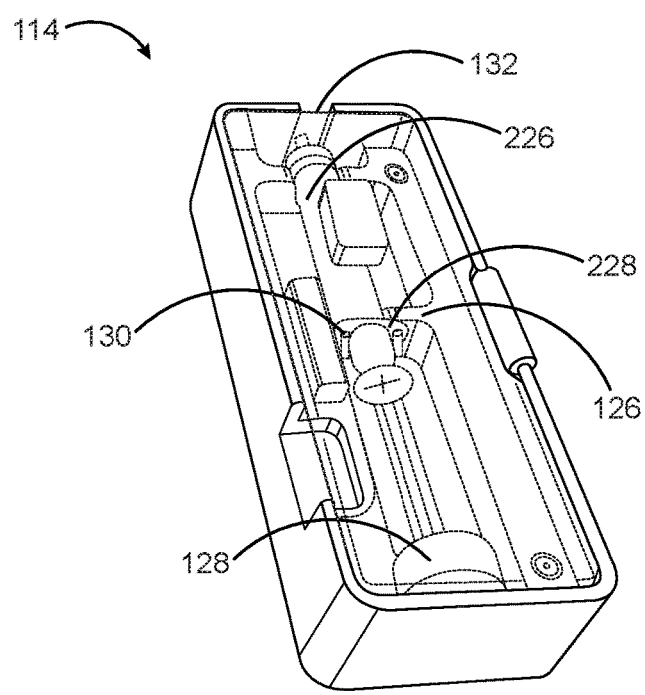
FIG. 22 illustrates a perspective view of the syringe pump module wherein a syringe is inserted in a syringe holder therein.

FIG. 17 illustrates the mixing module 110 in operation with the cryoprotectant mixing chamber 202 inserted therein, the freezing bag air expresser 112 at left, and the syringe pump module 114 at right in accordance with the preferred embodiment of the present invention. The operator has already sealed and detached the input tubing assembly 208 near the air filter 214. The cryoprotectant mixing chamber 202 is in the process of being mixed, the freezing bag air expresser 112 is in operation at the left and the syringe pump module 114 at right is shown with a syringe 226 inserted therein. The syringe pump module 114 includes the syringe holder 126, the actuator plunger 128 for actuating the syringe 226, the pair of retaining pins 130 and the syringe pump module door 132, which as shown in FIGS. 17-19 is closed. FIGS. 20 and 21 illustrate the syringe pump module 114 with the syringe pump module door 132 open and no syringe 226 inserted. FIG. 22 illustrates the syringe pump module 114 wherein the syringe 226 is shown locked into place in the syringe holder 126, and wherein the syringe pump module door 132 is transparent.

In the described method, the operator opens the syringe pump module door 132 by pushing on the door 132 and activating a spring loaded latch (not shown). The syringe 226 is filled with cryoprotectant solution and placed into the syringe holder 126. The syringe 226 is preferably loaded such that the flanges 228 of the syringe 226 are located beyond and are retained by the pair of retaining pins 130 such that when the syringe 226 is actuated, the entire syringe 226 will not move, but instead the syringe 226 will slowly dispense its contents. In a preferred embodiment, the actuator plunger 128 will not activate if the syringe pump module door 132 is open. Other suitable means for carefully and accurately dispensing a liquid solution may be employed, including electric pumps and gravity fed titration methods. The mechanism for the calculated and precise delivery of the cryoprotectant solution is thus variable.

Preferably, the cryoprotectant solution used is a DMSO/Dextran ($H(C_6H_{10}O_5)_xOH$) solution (hereinafter referred to as "DMSO solution"), wherein Dextran is used to cut the concentration of DMSO due to Dextran's low molecular weight and its propensity to surround the cell membrane and protect the membrane from the effects of water crystals formed during freezing and from the toxic effects of concentrated DMSO. Although Dextran is preferred, other suitable solutions such as other glucans and polysaccharides may be used in its place. Preferably the solution comprises up to 55% by weight per volume DMSO, up to 5% by weight per volume Dextran or similar, and the remainder of the solution comprises 0.9% weight per volume NaCl. In other embodiments, the DMSO solution may be up to 60% by weight per volume, Dextran may be present at up to 10% by weight per volume, with the remainder 0.9% weight per volume NaCl.

The syringe 226 at its tip includes a syringe extension tubing 230 and a syringe extension tubing cap (not shown). The syringe extension tubing 230 is connected to the cryoprotectant mixing chamber 202 via the cryoprotectant filter 204. The filter cap 206 is removed from the cryoprotectant filter 204 and the distal end of the syringe extension tubing 230 is attached to the cryoprotectant filter 204 such that the cryoprotectant solution is pumped out of the syringe 226 by the actuator plunger 128 and mixes with the harvested cell solution in the cryoprotectant mixing chamber 202 while the cryoprotectant mixing chamber 202 is moved due to the nutating motion of the mixing module 110.

The apparatus and associated method integrate a means of sterile passage of the cell solution through the freezing bag assembly 200 that is sterile connected and immune to the solvent action of the DMSO. The liquids introduced, such as the cryoprotectant solution introduced into the cryoprotectant mixing chamber 204 from the syringe 226, are not exposed to ambient air. During any time during the process where connections between components are introduced, such as when the syringe extension tubing 230 from the cryoprotectant solution filled syringe 226 is attached to the cryoprotectant mixing chamber 202, a filter is present to ensure system sterilization is maintained. In the case of the aforementioned connection, the cryoprotectant filter 204 ensures sterilization. Preferably, a two-tenths micron DMSO filter is employed to maintain the sterility. Other suitable filters can be used to achieve the sterility in alternative embodiments.

The temperature of the harvested cell solution inside the cryoprotectant mixing chamber 202 is carefully monitored as it is slowly lowered due to the cryoprotectant mixing chamber 202 being in contact with the cooling plate (not shown). Once the harvested cell solution is preferably between 4-6 degrees Celsius, the actuator plunger 128 begins to actuate the syringe 226 and dispense the cryoprotectant solution into harvested cell solution. A detection means (not shown) determines when air is being pumped and when cryoprotectant solution is being pumped through the syringe 226, such that the actuator plunger 128 moves relatively quickly when the air is pumped and slows considerably when the cryoprotectant solution is pumped. This ensures the entire process is not needlessly lengthened, but at the same time ensures the cryoprotectant solution is introduced to the cryoprotectant mixing chamber 202 at a slow and calculated and monitored rate. The syringe 226 continues to pump the cryoprotectant solution through the syringe extension tubing 230 and into the cryoprotectant mixing chamber 202 over the course of 5-30 minutes.

While the cryoprotectant solution is being dispensed into the cryoprotectant mixing chamber 202, the mixing module 110 is nutated back and forth to facilitate the rapid homogenous diffusion of the cryoprotectant solution to the harvested cell solution. An exothermic reaction begins to occur as the cryoprotectant solution contacts the harvested cell solution and introduces heat throughout the cryoprotectant mixing chamber 202. At the same time, the cooling plate (not shown) in the mixing module 110 draws this heat away through the bottom of the cryoprotectant mixing chamber 202 cooling the harvested cell solution diffused with the cryoprotectant solution. During the entire process, the temperature is carefully monitored, regulated and recorded. If the regulation fails and the temperature rises out of the range between 4-6 degrees Celsius, then the actuator plunger 128 ceases and the remaining cryoprotectant solution is not injected until the temperature falls back to within 4-6 degrees Celsius. Once the cryoprotectant solution is fully injected, the mixing module 110 will continue to mix and maintain a temperature until the next step.

By inserting the cryoprotectant solution at a specified rate and through the nutating mixing of the cell solution in the cryoprotectant mixing chamber 202 that assures no standing waves exist, a homogenous mixing process is substantially maintained. The final concentration of the cryoprotected cell solution in the cryoprotectant mixing chamber 202 preferably contains an approximately 10% concentration of cryoprotectant solution. In one exemplary embodiment, approximately 20 mL of blood is used, and approximately 5 mL of 10% cryoprotectant solution is added. In this exemplary embodiment, the cryoprotectant solution makes up 50% of the solution added, such that the total volume of cryoprotectant solution in the 25 mL of fluid is 10%. In other embodiments, less than 10% or greater than 10% cryoprotectant solution by volume of the final solution are described.

Due to the triangular shape of the cryoprotectant mixing chamber 202 and the nutating mixing of the mixing module 110, as each drop of the cryoprotectant solution is added to the cryoprotectant mixing chamber 202, it is very quickly distributed homogenously to the harvested cell solution. In use, this allows the cryoprotectant solution, to be added at a rate between 2x-3x the maximum rate as described in the prior art. Before the next step, the syringe extension tubing 230 is sealed and detached from the cryoprotectant mixing chamber 202 together with the syringe 226. The syringe 226 may be discarded.

Figure 23:
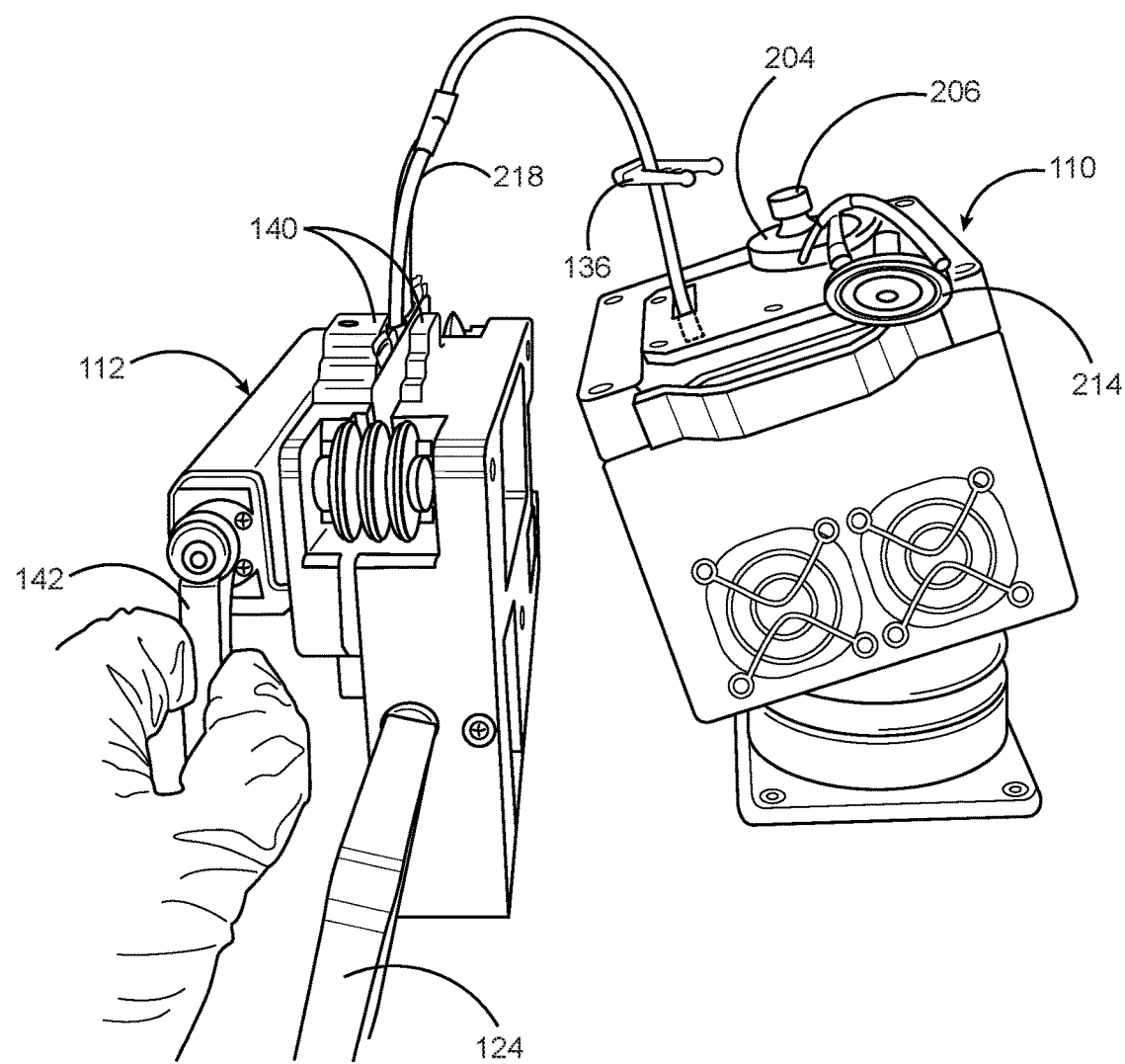
FIG. 23 illustrates a partial perspective view of a cryopreservation work station, illustrating a step wherein an operator rotating a handle on the freezing bag air expresser counter clockwise so as to substantially completely compress a freezing bag.

FIG. 23 illustrates a partial perspective view of a cryopreservation work station 100, illustrating a step wherein the operator rotates the handle 142 on the freezing bag air expresser 112 to express substantially all air from the freezing bag 220. The operator rotates the handle 142 on the freezing bag air expresser 112 counter clockwise so as to completely compress the freezing bag 220. The freezing bag 220 is appressed tightly between the pair of parallel walls 140 of the freezing bag air expresser 112. In an alternative embodiment, an automated clamping system is employed. The operator clamps the Y connector tubing 218 between the freezing bag 220 and the cryoprotectant mixing chamber 202 using the slide clamp or hemostat 136.

At the next step, the mixing module door 122 is opened and the cryoprotectant mixing chamber 202 is removed from the mixing module 110. The appressing pressure from the freezing bag air expresser 112 is removed, with the relative vacuum within the freezing bag 220 being maintained by clamping the Y connector tubing 218 connecting the freezing bag 220 and the cryoprotectant mixing chamber 202.

Figure 24:
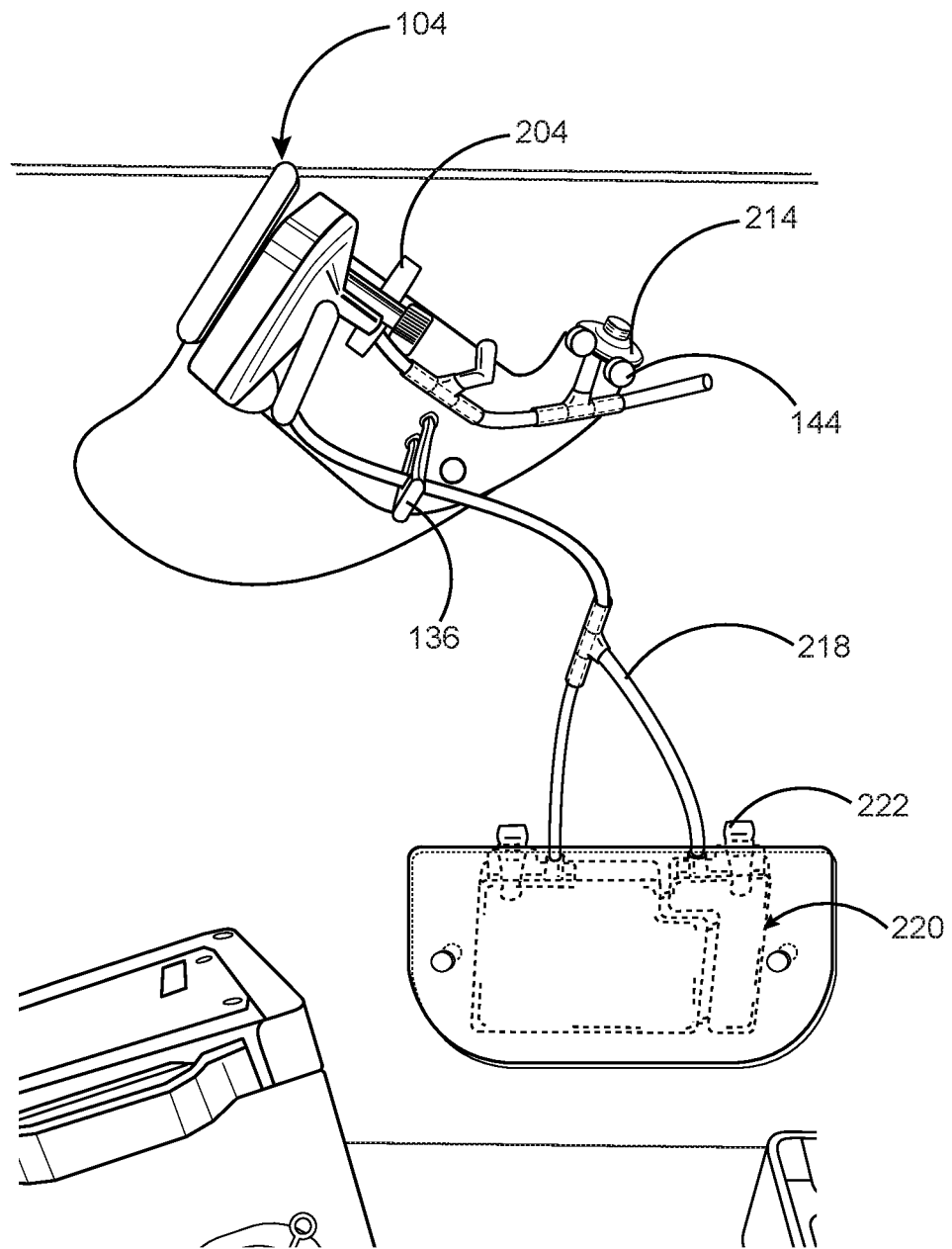
FIG. 24 illustrates a perspective view of the cryoprotectant mixing chamber placed in the upper mixing chamber holder such that a cryoprotectant filter is maintained in uppermost position and toward the operator, and the freezing bag in an empty condition.

Then, the freezing bag 220 is removed from the freezing bag air expresser 112. The cryoprotectant mixing chamber 202 is then placed in the upper mixing chamber holder 104 such that the cryoprotectant filter 204 is placed uppermost and toward the operator as shown in FIG. 24. The air filter 214 is placed into a filter hook 144 of the upper mixing chamber holder 104 and the freezing bag 220 is placed into the freezing bag holder 106.

Figure 25:
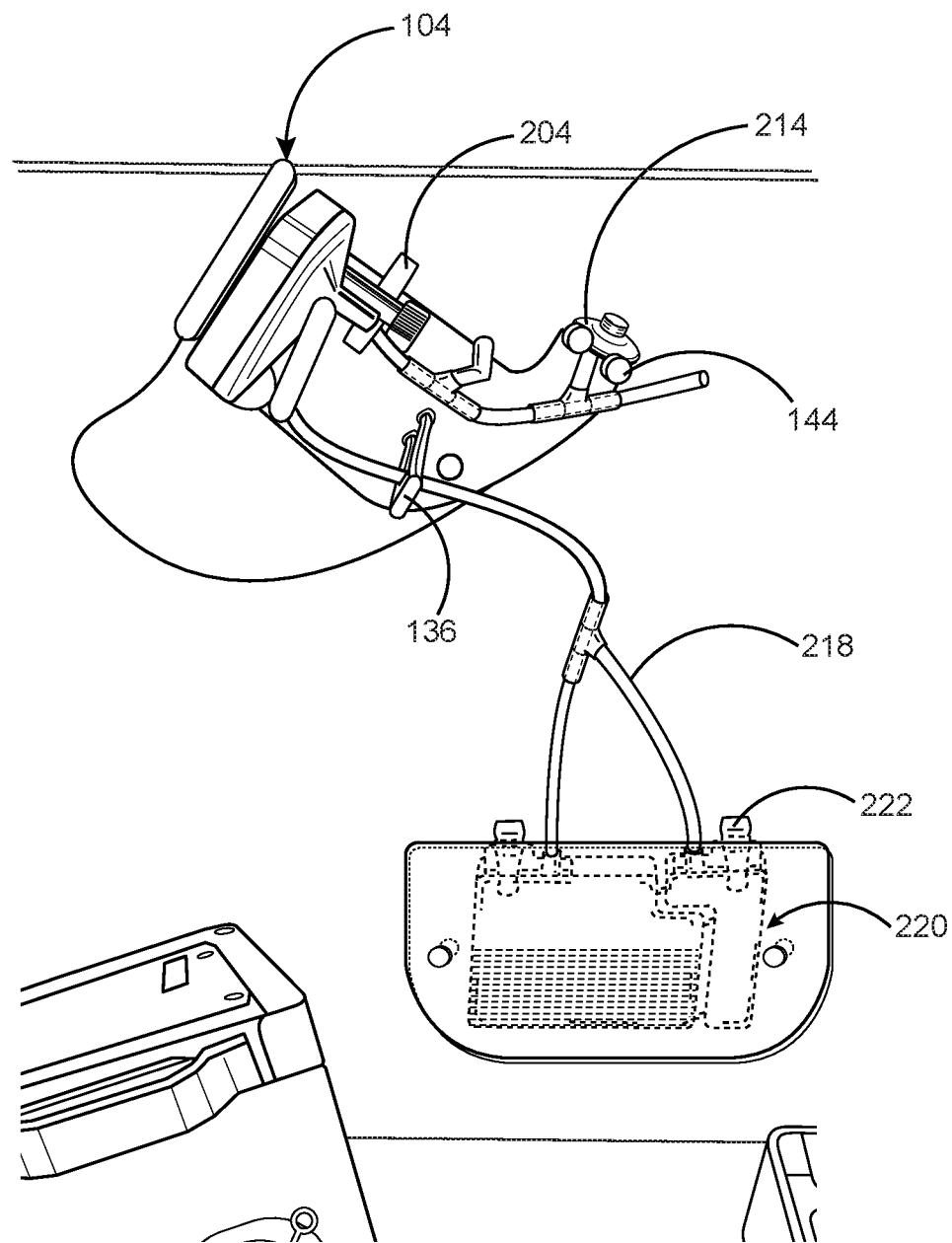
FIG. 25 illustrates a perspective view of the cryoprotectant mixing chamber placed in the upper mixing chamber holder such that the cryoprotectant filter is maintained in uppermost position and toward the operator, and the freezing bag partially filled with a cryoprotected cell solution.

In the preferred embodiment, the freezing bag 220 is two-chambered and comprises a large freezing bag chamber 234 and a small freezing bag chamber 236. At the next step, the slide clamp or hemostat 136 is removed from the Y connector tubing 218, thereby allowing the cryoprotected cell solution to flow from the cryoprotectant mixing chamber 202 into the freezing bag 220 as shown in FIG. 25, wherein the cryoprotected cell solution may be seen partially filling the large freezing bag chamber 234 in the two-chamber freezing bag 220. Because the air has been expressed from the freezing bag 220, an elastic moment is created in the freezing bag 220, which tends to facilitate the drawing in of the cryoprotected cell solution into the freezing bag 220 once the slide clamp or hemostat 136 is removed. Gravity from the positioning of the cryoprotectant mixing chamber 202 and the freezing bag 220 also assists the movement of the cryoprotected cell solution. The freezing bag holder 106 is configured to allow the elastic moment of the previously-compressed freezing bag 220 to return the freezing bag 220 to a state wherein the walls of the freezing bag 220 are substantially parallel to one another. As a result, upon long term storage in a freezing chamber, thermal contact between the sides of the freezing bag 220 and a canister in which the freezing bag 220 is placed will be even to provide uniform freezing.

The Y connector tubing 218 is sealed to create two equal segments 238, 240 on each line. When the cryoprotected cell solution flowing to the large freezing bag chamber 234 ceases, the slide clamp or hemostat 136 is placed on the first segment 238 of the Y connector tubing 218 leading to the large freezing bag chamber 234. The suction imparted on the cryoprotectant mixing chamber 202 from the elastic moment created in the small freezing bag chamber 236 further draws out additional cryoprotected cell solution therein. Finally, the operator places the slide clamp or hemostat 136 on the Y connector tubing 218 just upstream from the first segment 238 and the second segment 240.

Figure 26:
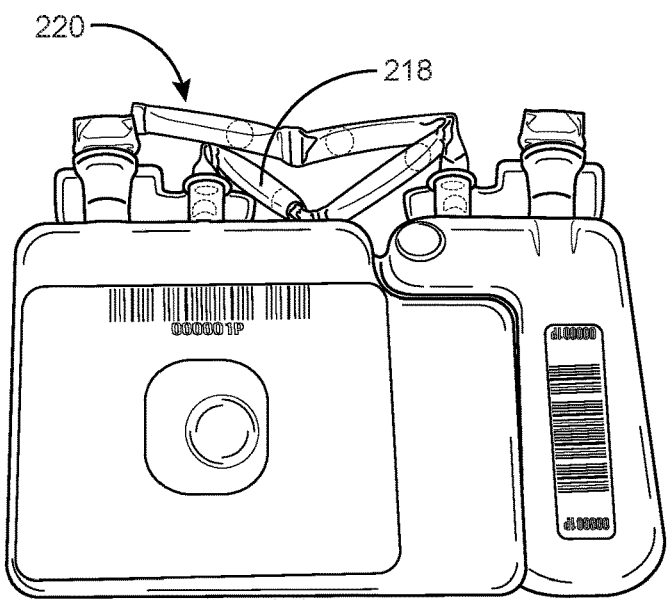
FIG. 26 illustrates a perspective view of a freezing bag filled with the cryoprotected cell solution.

FIG. 26 shows the freezing bag 220 filled with the cryoprotected cell solution and fully prepared for long-term cold storage in accordance with the preferred embodiment of the present invention. When the freezing bag 220 is filled with the cryoprotected cell solution, both the segments 238, 240 of the Y connector tubing 218 is sealed just below the bottom of the Y connector tubing 218 and removed from the freezing bag 220. In this and other embodiments, freezing bag 220 thus comprises multiple compartments each filled with solution yet fluidly disconnected from one another. No fluid connection between compartments allows for removal of one compartment without compromising the sterility of others.

Figure 27:
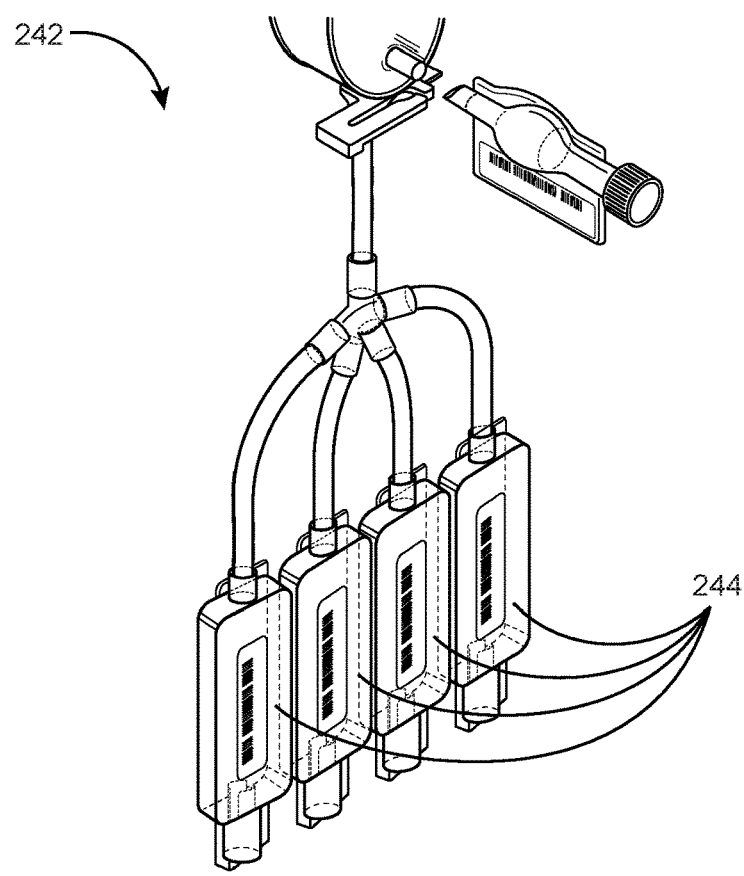
FIG. 27 illustrates a perspective view of a four-compartment freezing bag filled with the cryoprotected cell solution in accordance with an alternate embodiment of the present invention.

In some embodiments, multiple chambered freezing bags or single chamber freezing bags may be employed. FIG. 27 illustrates a perspective view of a four-compartment freezing bag 242 filled with the cryoprotected cell solution in accordance with an alternate embodiment of the present invention. The method of connecting the multiple compartments 244 is preferably small connecting tabs easily severable along an indent line placed in the tab during blow molding, equidistant from both compartments, both at room temperature and below, such as temperatures below −150° C. as expected after long term storage. While the bags are connected externally, no internal fluid connection exists. Thus, when separated by cutting at room temperature and snapping along the indent at the cryogenic temperatures, each compartment 244 provides minimal risk of breaching the individual compartments 244. Such joined compartments 244 are preferably composed of plastic that maintains its structural integrity following multiple transitions from cold temperatures, such as those associated with liquid nitrogen, to room temperature. Finally, the compartments 244 preferably provide a surface finish that allows adhesion by labels using adhesives approved by the Food and Drug Administration.

Figure 28:
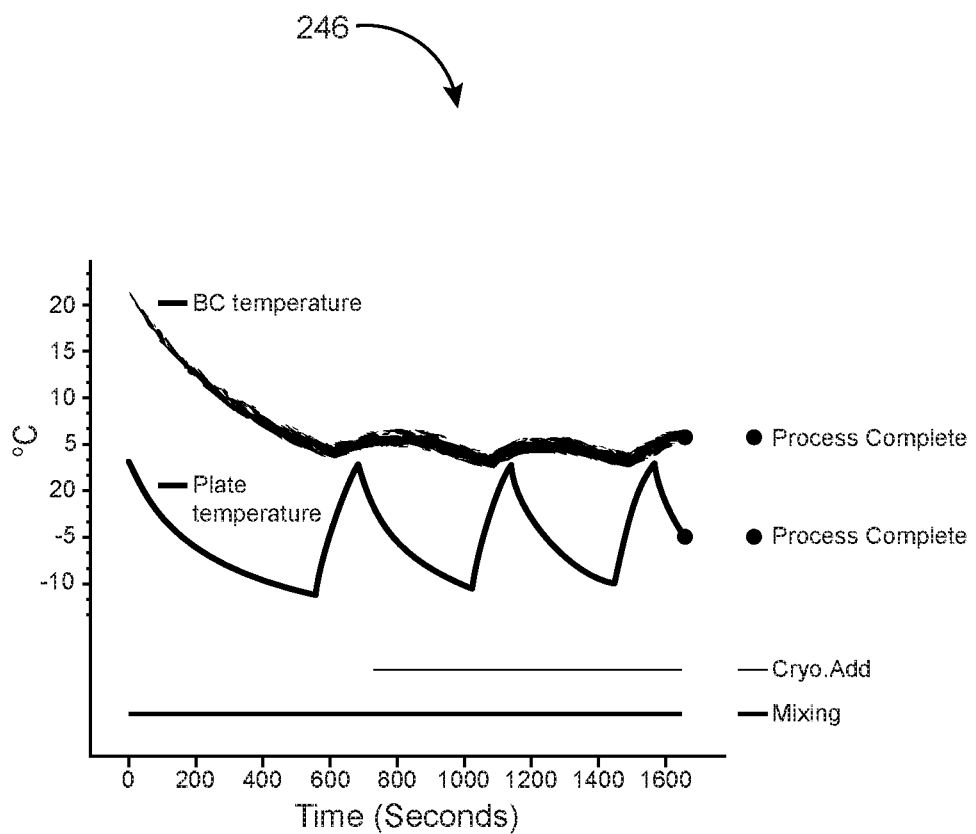
FIG. 28 illustrates an exemplary processing report showing data collected during an operation performed in accordance with the preferred embodiment of the present invention.

During the process described herein, and particularly during the cryoprotectant mixing chamber 202 mixing process wherein the cells are mixed with the cryoprotectant solution, the temperature of the cell mixture/cryoprotectant solution is carefully regulated, recorded and stored. For each execution of the steps of the method, the temperature of the surface of the mixing module 110 is also regulated, recorded and stored. The temperature of the cells is recorded, indirectly, by sending an infrared beam through the cryoprotectant mixing chamber 202. These temperatures are recorded before, during and after cryoprotectant solution insertion as shown by an exemplary processing report 246 at FIG. 28. Upon completion of one cycle of cryoprotectant insertion, an indicator 146 on the cryopreservation workstation 100 indicates that data is present. Preferably, the cryopreservation workstation 100 cannot run another cycle until the data is downloaded from the cryopreservation workstation 100 and stored to a secure storage server. This ensures that a record exists for every time the cryopreservation workstation 100 has been used, and ensures that data for every run is captured and stored.

The presently disclosed apparatus is advantageous because the recording of the data provides a real-time measurement of the temperature of the harvested cell solution before, during and after the insertion of the cryoprotectant solution. The exothermal heat release that occurs when the cryoprotectant solution is combined with the harvested cell solution is recorded. The recording of temperature extends beyond the completion of insertion of the cryoprotectant solution and provides a data trail from prior to the insertion of the cryoprotectant solution to the freezing and then storage stage of the cryoprotected cell solution. The documentation of the harvested cell solution, the cryoprotectant solution, and particular equipment used may be via known means in the art, such as the optical scanning of barcodes affixed to each component used during each step of the process.

When the temperature of the cells is carefully recorded during the cryoprotectant stage, and if that recording shows no increase in temperature, then an error occurring during that stage may be ruled out. Conventionally, post thaw colony forming assays may need to be performed in order to understand whether cell damage occurred. But the process described herein of recording the temperature of the harvested cell solution during the insertion of the cryoprotectant solution, eliminates the need for this conventional step.

During the process, the data is carefully recorded, including the temperature of the cooling plate and the harvested cell solution. This allows the insertion of the cryoprotectant solution to be safely maximized so that the heat release from the exothermic reaction is extracted substantially by the system to provide a substantially consistent, minimally varying temperature of the cell-cryoprotectant solution, which is represented by the exemplary processing report 246 at FIG. 28. Through this system of swift homogenization of the cryoprotectant solution, the rate of dissemination of the cryoprotectant solution is maximized, while cell death is minimized. The potential rate of the cryoprotectant solution insertion of the present invention while maintaining cell viability falls beyond a level disclosed or suggested by the prior art. Furthermore, and as described above, the apparatus and method provides a means of sterile passage of the cryoprotected cell solution from the beginning of the process to the completion in one or more sealable storage containers.

The foregoing description of the preferred embodiment of the present invention has been presented for the purpose of illustration and description. It is not intended to be exhaustive or to limit the invention to the precise form disclosed. Many modifications and variations are possible in light of the above teachings. For example, all the processes described in the method as performed by the operator or technician may be instead automated and/or otherwise performed automatically by the apparatus itself or a robotic assistant. It is intended that the scope of the present invention not be limited by this detailed description, but by the claims and the equivalents to the claims appended hereto.

What is claimed is:

1. A cryopreservation workstation for providing cryopreservation of biological materials in a sterile environment comprising:
   an upper platform;
   an upper mixing chamber holder;
   a freezing bag holder;
   a mixing module with a mixing chamber compartment comprising a mixing module cap, a cooling plate, a mixing module door, an infrared sensor to record the temperature of fluid contents within any fluid container placed within the mixing chamber compartment and a mechanism for nutating motion;
   a freezing bag air expresser to expel air from a three dimensional freezing bag, the freezing bag air expresser having a pair of parallel walls and a handle, and the freezing bag comprising multiple compartments not in fluid connection with one another;
   a cryoprotectant mixing chamber holder connected to the freezing bag air expresser;
   whereby the cryopreservation workstation provides mixing of contents of harvested cell solution and a cryoprotectant solution without the formation of standing waves, passage of cryoprotected cell solution under sterile conditions and monitoring, regulating and recording temperature of the cryoprotected cell solution.

2. The cryopreservation workstation of claim 1 wherein the upper platform includes at least one locking means that is configured to hold a rigid disposable cartridge filled with a harvested cell solution.

3. The cryopreservation workstation of claim 2 wherein the upper platform is tilted to provide a rocking motion of the rigid disposable cartridge thereby ensuring all cells resident in the harvested cell solution within the rigid disposable cartridge are contained in the harvested cell solution and not adhered to a compartment wall thereof.

4. The cryopreservation workstation of claim 1 wherein the mixing module door on a top portion of the mixing module is adaptable to seal a cryoprotectant mixing chamber inside the mixing chamber compartment of the mixing module.

5. The cryopreservation workstation of claim 4 wherein the cryoprotectant mixing chamber when placed within the mixing chamber compartment comes into contact with the cooling plate of the mixing module such that temperature of the harvested cell solution within the cryoprotectant mixing chamber is regulated by conduction due to direct heat transfer.

6. The cryopreservation workstation of claim 1 wherein the said multiple compartments of said freezing bag are severable along an indent line.

7. The cryopreservation workstation of claim 1 wherein the freezing bag comprises at least three compartments.

8. The cryopreservation workstation of claim 1 wherein the cryoprotectant solution is a dimethyl sulfoxide (DMSO) solution.

* * * * *